(12) United States Patent
Lawrence et al.

(10) Patent No.: US 7,291,481 B2
(45) Date of Patent: Nov. 6, 2007

(54) ASSAYS FOR TRICHOMONAL AND OTHER HYDROLASES

(75) Inventors: Paul J. Lawrence, Campbell, CA (US); Mark A. Hughes, Morgan Hill, CA (US); Aulena Chaudhuri, San Jose, CA (US); Terrence J. Andreasen, San Jose, CA (US)

(73) Assignee: Quidel Corporation, San Diego, CA (US)

( * ) Notice: Subject to any disclaimer, the term of this patent is extended or adjusted under 35 U.S.C. 154(b) by 0 days.

(21) Appl. No.: 11/353,497

(22) Filed: Feb. 13, 2006

(65) Prior Publication Data

US 2006/0127969 A1 Jun. 15, 2006

Related U.S. Application Data

(63) Continuation of application No. 10/269,917, filed on Oct. 10, 2002, now Pat. No. 7,041,469.

(51) Int. Cl.
*C12Q 1/02* (2006.01)
*C12Q 1/34* (2006.01)

(52) U.S. Cl. .......................................... 435/29; 435/18

(58) Field of Classification Search ...................... None
See application file for complete search history.

(56) References Cited

U.S. PATENT DOCUMENTS

| 5,416,003 A | 5/1995 | Lawrence et al. |
| 5,427,919 A | 6/1995 | Dennis et al. |
| 5,434,054 A | 7/1995 | Pollmann et al. |
| 5,571,684 A * | 11/1996 | Lawrence et al. ............. 435/18 |
| 5,663,044 A * | 9/1997 | Noffsinger et al. ............ 435/4 |

FOREIGN PATENT DOCUMENTS

EP 0254000 A1 1/1988

(Continued)

OTHER PUBLICATIONS

Schoonmaker, Judith N., et al. "A new praline aminopeptidase assay for diagnosis of bacterial vaginosis", *American Journal of Obstetrics & Gynecology* (1991) 165(3):737-742.

(Continued)

*Primary Examiner*—Ralph Gitomer
*Assistant Examiner*—Amanda P. Wood
(74) *Attorney, Agent, or Firm*—Townseend and Townsend and Crew LLP

(57) ABSTRACT

The release by trichomonads of a hydrolase that hydrolyzes a narrowly defined class of substrates at a low pH without interference from hydrolases that are unrelated to trichomoniasis is the basis for a selective diagnostic assay for trichomoniasis that measures hydrolysis of any of these substrates by vaginal fluid at a low pH. Selective assays for trichomoniasis are also obtained by removing particulate matter from a sample of vaginal fluid to extract a fraction devoid of particles greater than a selected size, and where desired, combining the extracted fraction with any of certain specified hydrolase inhibitors, then testing the fraction for enzymatic hydrolase activity. These qualities of trichomoniasis are the basis for a series of diagnostic tests and test devices that produce results that are detectable by visual and other means with a high degree of accuracy.

6 Claims, 7 Drawing Sheets

FOREIGN PATENT DOCUMENTS

| | | |
|---|---|---|
| EP | 0571939 A1 | 12/1993 |
| GB | 2378246 A | 5/2001 |
| WO | WO91/03544 A1 | 3/1991 |
| WO | WO96/15255 A2 | 10/1995 |

OTHER PUBLICATIONS

Garber, Gary E., et al. "Analysis of the extracellular proteases of *Trichomonas vaginalis*", *Parasitol Res.* (1994) 80:361-365.

Garber, Gary E., et al. "Characterization and purification of extracellular proteases of *Trichomonas vaginalis*", *Can. J. Microbiol* (1989) 35:903-909.

North, Michael J., et al. "The specificity of trichomonal cysteine proteinases analyses using fluorogenic substrates and specific inhibitors", *Molecular and Biochemical Parasitology*, (1990) 39:183-194.

\* cited by examiner

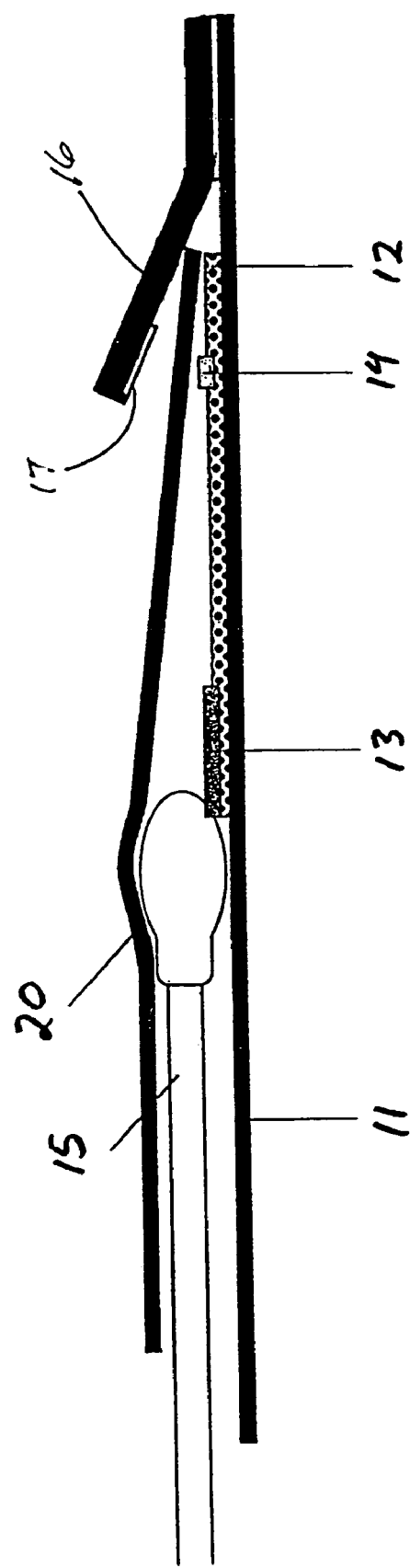

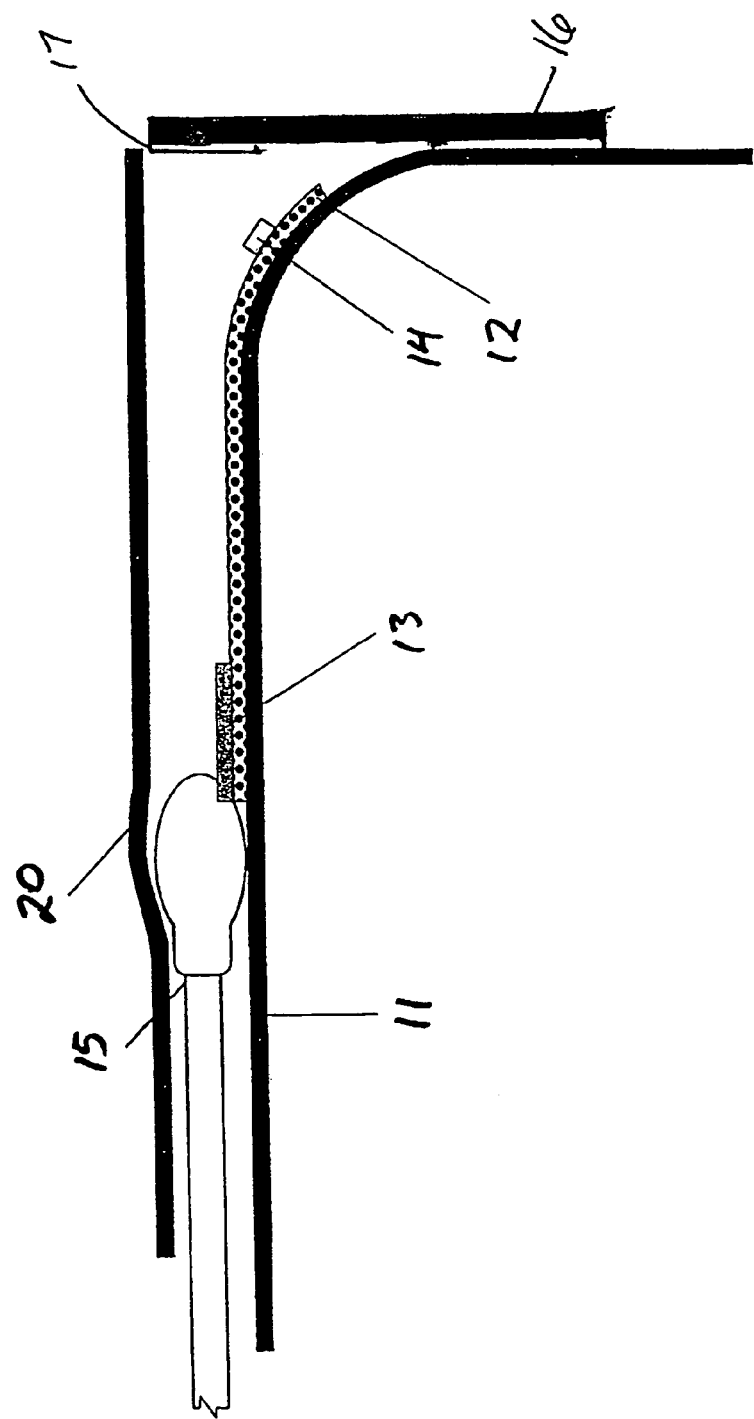

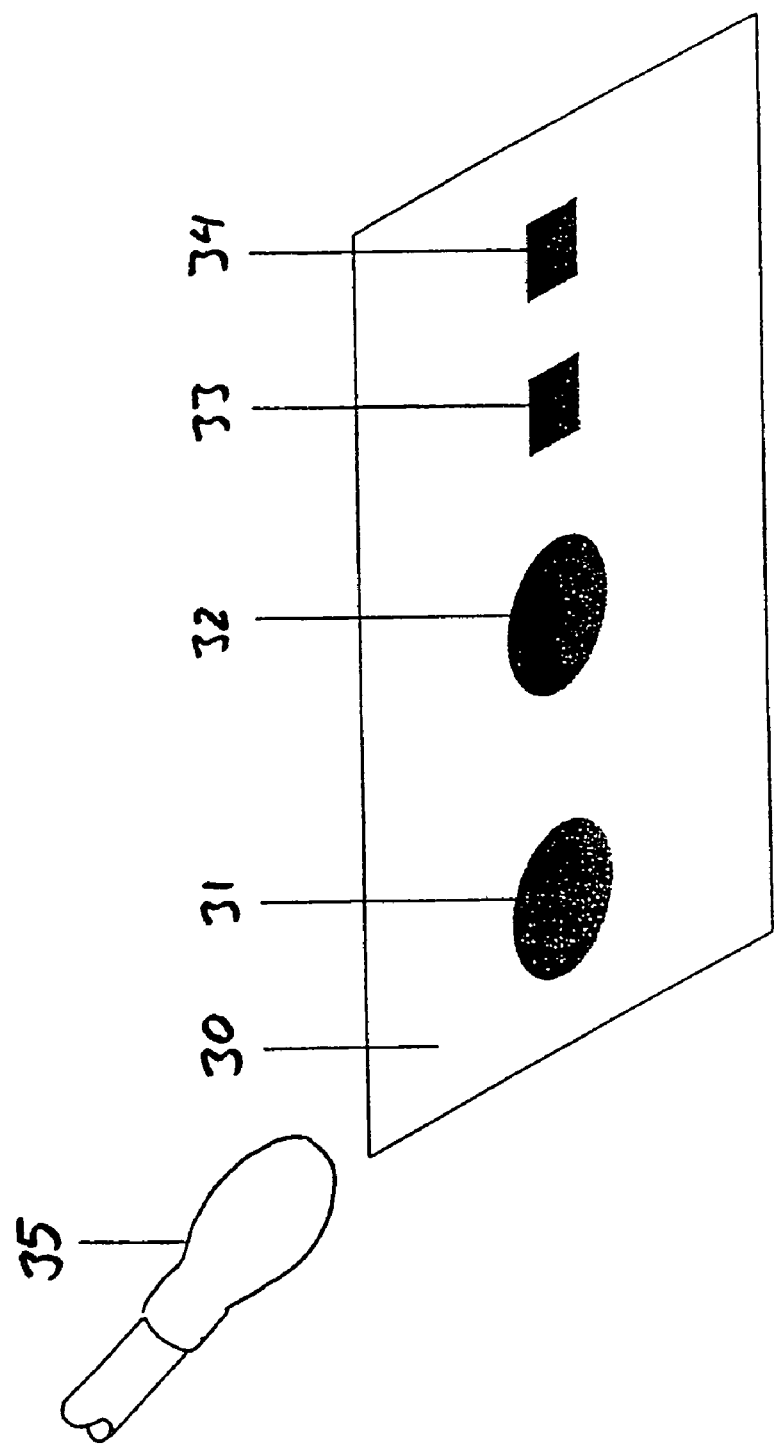

ASSAYS FOR TRICHOMONAL AND OTHER HYDROLASES

BACKGROUND OF THE INVENTION

1. Field of the Invention

This invention resides in the field of hydrolases (i.e., hydrolytic enzymes), and in particular, methods and devices for the detection of hydrolase activity in a sample or specimen and the diagnosis of disease based on the detection of hydrolase activity. A specific area of interest of this invention is the detection of trichomoniasis in female subjects by assaying for the presence of enzymatically active trichomonal hydrolases in a vaginal fluid specimen.

All literature cited in this specification, including patents, technical articles and books, are incorporated by reference in their entirety.

2. Description of the Prior Art

Trichomoniasis is a clinically important Sexually Transmitted Disease (STD) caused by the protozoan *Trichomonas vaginalis*. In 1955, the World Heath Organization estimated approximately 170 million new cases of trichomoniasis would arise annually among adults worldwide, with higher prevalence and incidence rates in both developing and industrialized countries than for any other sexually transmitted disease. Trichomoniasis is frequently undetected because most infected men and approximately 50% of infected women are asymptomatic. Trichomoniasis in women may cause discomfort or a foul smelling vaginal discharge, and can be associated with adverse clinical sequelae. Trichomoniasis can increase the risk the human immunodeficiency virus (HIV) transmission and infection (Laga et al., *AIDS* 7(1):95-102 (1993) and *WHO Press Release* WHO/64 (1995)).

Trichomonads produce specific hydrolases called proteinases that hydrolyze proteins including, but not limited to, IgG, IgM, and IgA antibodies (Provenzano and Alderete, *Infect. Immun.* 63(9):3388-3395 (1995)). These proteinases also damage secretory leukocyte hydrolase inhibitor (SLPI), a protective factor normally present in vaginal fluid that inhibits HIV viral entry into human monocytic cells (Draper et al., *J. Infect. Dis.* 178(3):815-819 (1998)). *Trichomonas vaginalis* (*T. vaginalis*) is also thought to play a role in promoting cervical cancer (Yap et al., *Genitourin. Med.* 71(6):402-404 (1995)). Pregnant women infected with *T. vaginalis* at mid-gestation are more likely to have a low birth weight infant or to deliver preterm (Cotch et al., *Sex. Transm. Dis.* 24:353-360 (1997)).

The most common method for diagnosing trichomoniasis is wet mount microscopy, a microscopic examination of vaginal fluid specimens for T vaginalis. This is a labor-intensive method which requires a microscope and a skilled technician, and fails to detect approximately half of the infected women (Baron et al., *Laboratory Diagnosis of Female Genital Tract Infections, Cumitech* 17A, American Society for Microbiology (1993)). Trichomoniasis can be diagnosed with high sensitivity by culturing vaginal fluid specimens, but this method requires culture media and long-term growth in a controlled-temperature incubator, in addition to the use of a microscope and a skilled technician. Due to the labor involved, the expense of culture media and supplies, the training required, and the delay of up to a week to detect trichomonal growth, few clinics or laboratories routinely use culture to diagnose trichomoniasis.

A diagnostic test based on DNA amplification and detection has recently been developed by Lawing et al., *J. Clin. Microbiol.* 38(10):3585-3588 (2000). This test is sensitive but, like culture, not rapid enough to produce the results during the patient's visit to the clinic. Due to the cost of the DNA-based test kits and the training and laboratory equipment required to perform these tests, this methodology is not widely used in clinics or in medical practice in general, particularly in the parts of the world where the need for a trichomoniasis test is greatest.

Thus, to date there is no rapid, accurate, cost-effective and simple method or test device for point-of-care diagnosis of trichomoniasis. Numerous studies have demonstrated that *T. vaginalis* produces a variety of hydrolases; see for example Garber et al., *Can. J Microbiol* 35:903-909 (1989). Two studies have demonstrated that vaginal fluid specimens from women with trichomoniasis contain detectable levels of hydrolases that disappear after infected women are treated and cured of the infection (Alderete et al., *Genitourin. Med.* 67(6):469 (1991), and Garber and Lemchuck-Favel, *Parasitol. Res.* 80(5):361-365 (1994)) Unfortunately, the laboratory-based hydrolase detection methods used in the studies reported by these authors required equipment, skill and training and were labor-intensive and slow, so that the results were obtained only after several hours. For example, the method used by Aldrete et al. for detecting trichomonal hydrolases involved a four-step process to produce gelatin-acrylamide zymograms: first, trichomonal hydrolases were electrophoretically concentrated into discrete bands in a sheet of polyacrylamide gel; second, the hydrolases were allowed to digest gelatin which had been immobilized within the polyacrylamide gel; third, the gel was stained with a general protein stain; and fourth, the gel was destained in a lengthy washing process which eventually revealed the hydrolase-digested gelatin which appeared as clear bands on the darkly stained background gel (the zymogram). Trichomonal hydrolases were detected in the Garber et al. study by polyacrylamide gel electrophoresis followed by immunoblotting, a similarly complex procedure that involved the use of rabbit antibodies to visualize a specific hydrolase band. Both methods require a high level of expertise and costly equipment and take many hours to complete, and are therefore unsuitable for point-of-care testing.

The zymogram procedure described above can also be performed by using synthetic fluorogenic substrates to detect the trichomonal hydrolases once the hydrolases have been separated by gel electrophoresis. These substrates typically contain one or more amino acids linked to a fluorogenic reporter group that becomes fluorescent only after it is enzymatically cleaved from the peptide group by a hydrolase. Unfortunately, this procedure still entails the unwieldy polyacrylamide gel electrophoresis step prior to testing for hydrolase activity with the fluorogenic substrates. Moreover, hydrolysis of the substrate can be observed only by examining the electrophoretic gels for bands that fluoresce under ultraviolet light. Both the gelatin-digestion method and the fluorogenic substrate method were utilized in a study of intracellular and secreted *T. vaginalis* hydrolases reported by North et al., *Mol. Biochem. Parasitol.* 39:183 (1990). Several fluorogenic substrates were identified which could be used to detect trichomonal hydrolases. Unfortunately, the methods used in this study are impractical for a point-of-care clinical diagnostic test, since gel electrophoresis is slow and cumbersome and observation of fluorescence requires instrumentation or a darkroom and ultraviolet illuminator. The difficulty is that vaginal fluid contains many different hydrolases secreted by a variety of sources, including bacteria, which are present at extremely high levels, white blood cells, vaginal epithelial cells, and others. Each method relies on electrophoretic separation to achieve selective detection of the trichomonal hydrolases. Without electrophoretic separation, it could not be determined if the hydrolytically active bands were derived from trichomonads or from some other source of hydrolytic activity in a vaginal fluid specimen.

A trichomoniasis test is therefore needed that can be performed by attending clinicians quickly, simply, inexpensively and accurately while the patient is still present. It would be particularly beneficial to be able to perform the test with a disposable device that is inexpensive and easy to use and one that rapidly produces accurate results.

SUMMARY OF THE INVENTION

A series of discoveries has now been made that permit a sample of vaginal fluid to be tested for the presence of *T. vaginalis* in a fast, accurate, and efficient manner. These discoveries also lead to methods and test devices for detecting the presence of enzymes in general, including various types of hydrolases, that are indicative of a variety of physiological conditions. The specimens in which the detections are performed may be any bodily fluids, vaginal fluid being but one example.

One discovery is that trichomonads release a particular hydrolase into vaginal fluid that actively hydrolyzes a narrowly defined class of substrates at a low pH without interference from other hydrolases that are unrelated to trichomoniasis and that are also present, or frequently present, in vaginal fluid. A diagnosis of trichomoniasis can thus be made by assaying vaginal fluid for hydrolytic activity against one or more members of this class of substrates at low pH. Hydrolysis of the substrate is readily converted to a signal that is either machine-readable or visually detectable.

This discovery can be implemented in various diagnostic methods and test materials. One example is the use of an implement that is capable of retaining liquid together with a solid support on whose surface are deposited the assay components, in distinct regions if necessary, depending on the particular assay methodology. The implement can be applied to the surface and the assay result can be read directly on or in the implement. The implement can for example be a swab, dropper, pipette, or other liquid transfer device, and the deposited assay components can include a substrate and an indicator. Swabs are particularly convenient implements since a swab can easily be wetted with the sample, then rubbed on the operative surface of the solid support, causing the assay components deposited on the surface to adhere to the swab. This allows the user to perform the assay determination by simply noting whether a detectable change, preferably a color change, has occurred on the swab.

A further discovery is that trichomonal hydrolase activity, without being restricted to low pH, can be separated from other sources of hydrolase activity in a specimen of bodily fluid by size exclusion. Thus, by extracting from a specimen of bodily fluid, particularly vaginal fluid, a fraction that is devoid of particulate matter above a certain size threshold, one can detect the presence or absence of trichomoniasis in the specimen by determining whether hydrolytic cleavage of the substrate has occurred. Selectivity toward trichomonal hydrolase activity can be improved further by combining size exclusion with the use of a narrowly defined class of hydrolase inhibitors. Thus, in preferred embodiments of this discovery, a sample of vaginal fluid is processed to extract a fraction that is devoid of particulate matter above a certain size threshold and, in the presence of one or more of these inhibitors, the extracted fraction is brought into contact with an appropriate substrate to detect hydrolase activity. Restricting the substrate to a narrowly defined class provides even greater selectivity for trichomonal hydrolase activity.

Related to the discovery addressed in the preceding paragraph is the discovery of a test device that includes a migration path through which a sample of bodily fluid that is applied to the device travels by capillary force. The device contains porous material along the migration path to filter out particulate matter above a selected size threshold. The device is useful for the detection of any soluble enzyme that is not adhered to cells or other particulate matter in the bodily fluid, and bodily fluids on which the device can be used include vaginal fluid, urine, blood, saliva, and various others. The device also contains a substrate that is acted upon by the enzyme of interest and an indicator that produces a signal as a result of action of the enzyme upon of the substrate. In assays for trichomoniasis, for example, the substrate will be one that is hydrolyzed by trichomonal hydrolase activity. An alternative to the substrate-indicator combination is a substrate that includes a chromogen that undergoes a color change as a direct result of the action of the enzyme of interest. For enzymes that cause cleavage of the substrate, the chromogen may undergo a color change upon release of the chromogen from the remainder of the substrate. Hydrolases, including trichomonal hydrolases, are examples of such enzymes. Regardless of whether a substrate-indicator combination is used or a substrate is used that includes a chromogen whose color changes upon action of the enzyme, the substrate, the indicator if one is present, or both substrate and indicator are positioned far enough along the migration path that the visual signal is attributable only to hydrolytic activity in the filtered liquid. In preferred such devices, one of the class of inhibitors referred to above is also included to further improve the selectivity of the assay.

Among the advantages that are offered by these discoveries, methods, compositions and devices are accuracy and selectivity in the diagnosis of *T. vaginalis*, tests that can be performed quickly with minimal training or instruction, and the ability to perform the tests in test devices that are self-contained with all reagents included and requiring only the application of the liquid test specimen. These and other objects, features, aspects, and advantages of the invention, as well as various embodiments of the principles forming the basis for the various discoveries, will be apparent from the description that follows.

BRIEF DESCRIPTION OF THE DRAWINGS

FIGS. 3a, 3b, 3c, and 3d are vertical cross sections of a third test device in accordance with this invention, representing a further variation on the test devices of FIGS. 1 and 2.

FIG. 4 is a perspective view of a fourth test device in accordance with this invention, in which the test result is observed on a swab that has been wetted with a specimen of vaginal fluid and then applied to the device.

DETAILED DESCRIPTION OF THE INVENTION

Figure 1:
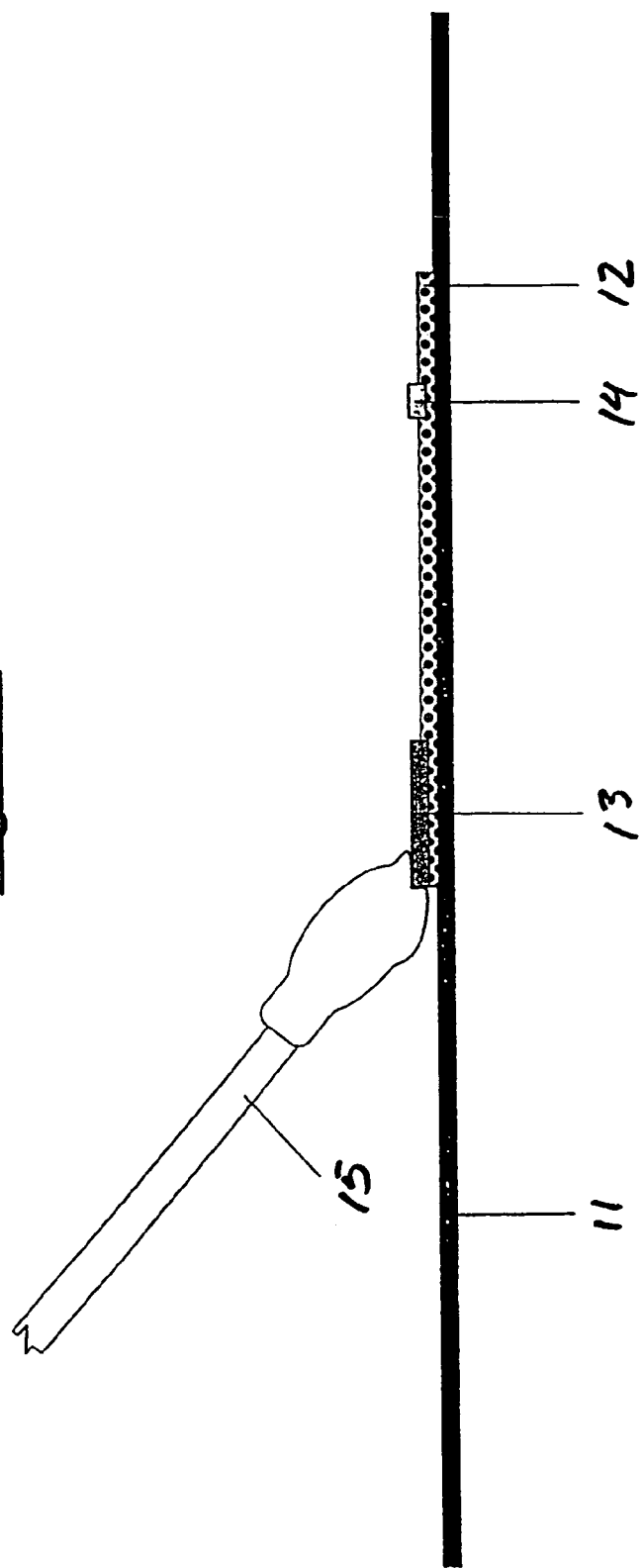
FIG. 1 is a vertical cross section of a test device in accordance with this invention, in which the test result is read on the test device itself.

In embodiments of the invention in which a sample of vaginal fluid is assayed for hydrolytic activity at low pH using a selective class of hydrolase substrates, the low pH is preferably within the range of 2 to 3.5, and most preferably within the range of 2.3 to 2.4. To perform the assay at a pH within these ranges, a sample of vaginal fluid must typically be acidified to place its pH within these ranges, since the sample as first taken may have a pH anywhere within the range of approximately 3.8 to approximately 6.5. Acidification can be accomplished at various different stages, such as acidifying the sample before contact of the sample with the substrate, acidifying the substrate before contact of the sample with the substrate, or acidifying the sample, substrate, or both while contacting the sample with the substrate. One method of acidification is dilution of the sample with an aqueous solution of an acidic buffer to bring the sample to the desired pH, followed by contacting the acidified sample with the substrate. The acidic buffer can be either in liquid form or in solid form, and examples of acidic buffers are malic acid, glycine, lysine, and threonine. Of these, malic acid and threonine are preferred. A particularly preferred buffer is 200 mM threonine adjusted to pH 2.3 or 2.4.

In various embodiments of the invention, the substrate is a conjugate consisting of a residue covalently bonded to a reporter group, the covalent bond being cleavable by hydrolytic enzyme activity. The term "reporter group" is used herein to denote any group that creates, causes, or leads to the generation of a detectable signal upon release from the residue. For the embodiments described in the preceding paragraph, the preferred conjugate includes as the substrate residue a peptide whose C-terminus is either arginine or lysine while the reporter group is a species that produces a detectable change upon hydrolytic cleavage from the peptide, the hydrolytically cleavable covalent bond being at the C-terminus of the peptide. Examples of linkages that contain hydrolytically cleavable bonds are amide linkages and ester linkages. The reporter group can thus be bonded to the substrate residue through either of these two linkages. The detectable change occurs either in the reporter group itself or in a separate indicator with which the reporter group comes into contact during the course of the assay. The peptide is preferably 1 to 6 amino acids in length, and most preferably 2 to 3 amino acids in length, and the preferred amino acid at the C-terminus is arginine. To assure that the hydrolysis occurs at the C-terminus, the N-terminus of the peptide is preferably blocked with an N-blocking group. Examples of N-blocking groups are carbobenzoxy, benzoyl, t-butoxycarbonyl, and D-amino acids. Other examples will be apparent to those skilled in the art.

The detectable change can be either visually readable by a clinician performing the test or self-readable by one who is performing the test on oneself, or machine-readable by instrumentation that detects the change and optionally performs additional functions, such as for example comparing the result to control values or to a calibrated scale, quantifying the result, performing two or more different tests on a single specimen, or performing the same test simultaneously on a multitude of samples and developing either statistical data from the results or simply recording them in a systemized manner.

The conversion that is caused by the cleavage of the reporter group from the substrate residue and that leads to the detectable change can be either a chemical transformation or a spatial relocation. In embodiments where the detectable change results from chemical transformation, the inability of the reporter group to produce a detectable signal when coupled to the substrate residue can for example be the result of a chemical neutralizing effect of the residue on the reporter group, which effect is eliminated when the linkage is cleaved. In embodiments where the detectable change results from spatial relocation, one example is the use of a substrate whose residue is permanently coupled to an inert surface on the test device and an indicator that is also permanently coupled to an inert surface on the test device but at a location spatially separated from the substrate residue. When a liquid sample is added that wets both the substrate and the indicator and contains the enzyme of interest, the reporter group is cleaved from the substrate residue and migrates through the liquid sample to the indicator to produce the detectable change. Other examples will be readily apparent to those skilled in the art. In all of these examples, the cleavage of the linkage between the substrate residue and the reporter group can occur by the direct action of the trichomonal hydrolase on the linkage or by the action of the trichomonal hydrolase in combination with other hydrolases.

Reporter groups that produce a visually detectable color change are preferred. One type of reporter group that produces a visually detectable color change is a compound that reacts with an indicator to cause a color change in the indicator. To assure that the color change results from hydrolytic cleavage of the reporter group from the remainder of the substrate (i.e., the substrate residue), the substrate and indicator can be immobilized at spatially separated locations in a test device in a manner rendering them insoluble in the sample, with the reporter group migrating or otherwise flowing toward the indicator only after the reporter group has been cleaved from the substrate residue. Another type of reporter group that produces a color change is one that itself changes color upon release from the substrate residue, i.e., upon cleavage of the covalent bond joining the reporter group to the substrate residue. After hydrolytic release from the substrate residue, the reporter group can be restrained or immobilized by chemical or mechanical means to confine the color signal in a defined region in the device.

Indicators that will display a color change when reacted with an appropriate reporter group include, but are not limited to, para-dimethylamino-cinnamaldehyde (pDMAC), diazonium salts, and tetrazonium salts. Examples of specific dyes within these classes are Fast Garnet GBC, Fast Dark Blue G, Fast Red B, Fast Red RL, Fast Corinth V, Fast Bordeaux GB, Fast Violet B, and Fast Black K. Each of these indicators is colorless or lightly colored in its unreacted state, and forms a highly colored derivative when reacted with reporter groups such as phenols, naphthols, aromatic amines or structural analogs of such reporter groups. Further examples of diazonium and tetrazonium salts and descriptions of their use are found in Conn, H. J., *Biological Stains*, R. D. Lillie, M. D., ed., Baltimore: The Williams & Wilkins Co., Ninth Edition (1977), pp. 200-224. Diazonium dyes are particularly useful examples.

As noted above, examples of linkages between the reporter group and the substrate residue that are cleavable by hydrolases are amide linkages and ester linkages. The reporter groups can therefore be amines or hydroxyl compounds analogous to the amines. Examples of amines useful for this purpose are 4-methoxy-2-naphthylamine, β-naphthylamine, and 7-amino-4-methylcoumarin. Examples of hydroxyl compounds useful for this purpose are α-naphthol, β-naphthol, 3-hydroxy-2-naphthoic acid, 6-hydroxy-2- naphthoic acid, 6-hydroxy-2-naphthalenesulfonic acid, 1-naphthol-3,6-disulfonic acid, 6-bromo-2-naphthol, 6-hydroxy-2-naphthyl disulfide, and 4-hydroxy-1-naphthalenesulfonic acid.

Amino acids can serve as reporter groups that can produce detectable changes in a wide variety of indicators, either directly or indirectly. Examples of indirectly generated color changes are chromogenic systems in which the amino acid reporter group reacts with oxygen in the presence of an amino acid oxidase to produce hydrogen peroxide and an oxidized amino acid, and the hydrogen peroxide then reacts with a reduced chromogen in the presence of a redox catalyst to produce color. Chromogens that can be used in this manner include, but are not limited to, guaiac, 2,2'-azino-bis(3-ethyl-benzthiazoline-6-sulfonic acid), tetramethylbenzidine, mixtures of phenol and 4-aminoantipyrine, and 4,5-dihydroxy-naphthalene. Examples of redox catalysts are peroxidases, iron protoporphyrin and metal ions. Any amino acid capable of being oxidized by oxygen in the presence of an amino acid oxidase to produce hydrogen peroxide can be used. Examples are alanine, leucine, serine, phenylalanine, aspartic acid, and tyrosine.

Examples of substrates with reporter groups meeting the above descriptions are carbobenzoxy-L-valine-L-arginine-4-methoxy-2-naphthylamine, carbobenzoxy-L-arginine-L-arginine-4-methoxy-2-naphthylamine, carbobenzoxy-L-arginine-L-arginine-L-arginine-4-methoxy-2-naphthylamine, carbobenzoxy-L-leucine-L-arginine-4-methoxy-2-naphthylamine, carbobenzoxy-L-valine-L-arginine-4-methoxy-2-naphthylamine, and D-valine-L-leucine-L-arginine-4-methoxy-2-naphthylamine. Among these, the most preferred are carbobenzoxy-L-arginine-L-arginine-L-arginine-4-methoxy-2-naphthylamine and D-valine-L-leucine-L-arginine-4-methoxy-2-naphthylamine.

Reporter groups that produce a color change directly upon release from a substrate residue include, but are not limited to, such species as indoxyl and pH indicators such as chlorophenol red and tetrabromophenolphthalein ethyl ester. Indoxyl, for example, forms a colorless conjugate when attached to a substrate residue, and yet upon release from the residue reacts with atmospheric oxygen to form an intense blue color (indigo). Chlorophenol turns red upon release from a residue when the pH is above the transition point of chlorophenol red, and tetrabromophenolphthalein ethyl ester turns blue upon release from a residue when the pH is above its transition point. Other examples will be apparent to those with experience in the use of pH indicators. The choice of pH indicator will depend in part on the pH at which enzyme activity is detected, i.e., for those embodiments in which a low pH is necessary the appropriate pH indicators will be those whose transition points are within the same low range as that in which the assay is conducted. For those embodiments in which the pH is not restricted to a low range, pH indicators with higher transition points can be used.

In embodiments of the invention that utilize size exclusion to achieve selective detection of trichomonal hydrolase activity, the removal of particulate matter, including non-specific enzymatically active particular matter, results in the removal of a major portion of the interfering enzymatic activity in the fluid without eliminating the soluble or non-particulate hydrolytic activity that is attributable to the presence of T. vaginalis. The size threshold, i.e., the smallest particles that are removed from the fluid by the size exclusion, is preferably 20 microns, more preferably 10 microns in diameter, and most preferably 1 micron in diameter. The size exclusion thus preferably results in a fraction that is devoid of all particles greater than 20 microns in diameter, more preferably devoid of all particles greater than 10 microns in diameter, and most preferably devoid of all particles greater than 1 micron in diameter. Size exclusion can be achieved by conventional methods, including centrifugation, filtration (both pressure filtration and vacuum filtration), sedimentation, and precipitation. A particularly convenient method of achieving size exclusion is by the use of a test device that includes a solid chemically inert porous material that serves as a filter medium, arranged in the device in such a manner that the liquid sample passes laterally through the porous material before reaching the test zone in which the enzymatic activity of the sample is tested. The test device can thus be designed to include an application site designated for entry of the sample, a test site where enzymatic activity either occurs or is detected, and a lateral flow path between the application site and the test site for movement of the sample either by capillary action; pressure differential, gravity flow, or any other driving force, with the porous material either filling or traversing the flow path. One particularly convenient configuration of the porous material is a continuous elongated strip arranged such that capillary action draws the sample lengthwise along the strip.

To further exclude enzymatic activity that is not attributable to trichomonal hydrolases or to other hydrolases to which the assay may be directed, the assay can be performed in the presence of one or more of a series of hydrolase inhibitors that are specifically chosen to isolate the hydrolase of interest. In assays for the detection of trichomonal hydrolase activity, these inhibitors include antipain, chymostatin, trans-epoxysuccinyl-L-leucylamido-(4-guanidino)butane, and various polypeptides and dipeptides including Lys-Pro-Gln-Leu-Trp-Pro, Arg-Lys-Asn-Val-Tyr, and Lys-Pro. In certain cases, the amount of inhibitor present will affect its selectivity, i.e., its ability to inhibit the enzyme (including hydrolase) activity that is not attributable to trichomonal or other target hydrolases without inhibiting the target hydrolase activity. This is generally a matter of degree, since in some cases there may be inhibition of all hydrolase activity to some extent and to varying degrees from one hydrolase to the next, and some inhibition of the target hydrolase activity can be tolerated while still producing a viable assay. The amount of any particular inhibitor that will result in preferential inhibition of the non-target hydrolase activity to an extent sufficient to produce a reliable assay is readily determinable by routine experimentation well within the routine skill of the laboratory technician. For selective inhibition of interfering, non trichomonal hydrolase activity, antipain, for example, is used at a preferred concentration range is 5 micrograms/mL to about 40 micrograms/mL, and for chymostatin, a preferred concentration range is from about 0.2 mM to about 10 mM.

As in the embodiments of the invention that require a low pH, the substrate in embodiments that employ size exclusion and hydrolase inhibitors can be a conjugate that consists of a reporter group bonded to a substrate residue by a covalent bond that is cleavable by hydrolysis, the reporter group being a species that produces a detectable change in an indicator upon contact with the indicator. When a substrate of this type is used, the substrate and the indicator are placed in individual, spatially separated regions in the test device, and the device is constructed to cause the sample to contact the two regions in succession, ultimately placing the released reporter group in contact with the indicator. According to one such arrangement, the indicator region is placed upstream of the substrate region relative to the direction of flow, and the indicator is soluble in the sample while the substrate is either fixed in position and poorly soluble in the sample or simply placed downstream such as at the end of the porous strip that constitutes the test device. In this arrangement, only the indicator travels with the sample flow. In an alternative arrangement, the positions are reversed. In either arrangement, the indicator can be any species that produces a detectable signal, whether machine-readable or visually detectable, and whether directly or indirectly through other (intermediary) species. Preferred indicators are those that produce a visually detectable signal such as fluorescence, chemiluminescence, or a simple color change. The reagent is likewise any species that causes the change in the indicator to occur. Examples of visually detectable indicators are p-dimethylaminocinnamaldehyde, diazonium dyes, and tetrazonium compounds, although many others are known to those skilled in the art and can be used in these assays. The individual indicators listed above are specific examples that can be used here as well. Preferred reporter groups are those that react with the indicator in the most intense and efficient manner. Examples of reporter groups useful for this purpose are 4-methoxy-2-naphthylamine, beta-naphthylamine, and 7-amino-4-methylcoumarin, and analogs and derivatives of these materials, α-naphthol, β-naphthol, 3-hydroxy-2-naphthoic acid, 6-hydroxy-2-naphthoic acid, 6-hydroxy-2-naphthalenesulfonic acid, 1-naphthol-3,6-disulfonic acid, 6-bromo-2-naphthol, 6-hydroxy-2-naphthyl disulfide, and 4-hydroxy-1-naphthalenesulfonic acid.

Another type of substrate that can be used in these embodiments that employ size exclusion and selective hydrolase inhibitors is a conjugate of a chromogen bonded to a binding member by a covalent bond that is cleavable by hydrolysis, the chromogen being a species that itself undergoes a detectable change upon release from the binding member. The description of chromogens presented above in connection with embodiments of the invention that focus on hydrolytic activity at low pH is applicable to these embodiments as well.

Still further selectivity toward trichomonal hydrolase activity in embodiments of the invention that utilize size exclusion and one or more of the inhibitors mentioned above can be achieved when the binding member of the conjugate described in the preceding paragraph is a peptide bonded to the reagent at the C-terminus of the peptide, with either lysine or arginine as the amino acid at the C-terminus. Preferred peptides are those of 1 to 6 amino acids, while the most preferred are those with 2 to 3 amino acids. It is also preferred that the N-terminus of the peptide be protected against hydrolysis by an N-blocking group, examples of which are cited above.

In certain implementations of the invention, the performance of the test will benefit by diluting the sample of bodily fluid with an aqueous diluent before applying the sample to the test device. Dilution of the sample can lower the viscosity of the sample to improve its flow characteristics. The diluent can also provide a means of controlling the pH of the sample in cases where the test results may vary with the sample pH. Thus, the preferred diluents in many cases are aqueous solutions of buffering agents, particularly those that stabilize the diluted sample at a pH of from about 6.5 to about 7.5. One such buffering agent is imidazole; others will be readily apparent to those skilled in the art.

While the descriptions above are directed primarily to assays of vaginal fluid specimens, the methodologies of this invention are useful in the detection of a variety of hydrolases or other target enzymes that can be detected in different bodily fluids, such as blood, urine, saliva, and cerebrospinal fluid. Assays for *Trichomonas vaginalis* are best conducted on vaginal fluid specimens.

Test devices are readily designed to contain the features that characterize each the assays and embodiments described above. The preferred test devices are those that contain all components of the assay in solid dry form, requiring only the application of a specimen of bodily fluid and at most a minimal number of additional reagents or components. In particularly preferred embodiments, the test device is entirely self-contained, requiring only the application of the specimen, either at full strength or diluted with an aqueous buffer solution. Application of the specimen can achieved by an appropriate transfer implement, such as a swab, a finger cot, a cervical brush, a dropper, or a pipette or other type of aspiration tube, or generally any device that can be used to collect and transfer the specimen, or by methods such as a vaginal wash. Swabs may consist of cotton, Dacron, or any other natural or synthetic absorbent material affixed to a handle made of plastic, wood, or other rigid material.

The test device will be designed to allow detection of the change that indicates the presence of hydrolase activity as an immediate or quick response to the application of the specimen. In some cases the detectable change can be read or observed, and quantitated if desired, on the implement used to apply the sample, while in others the change can be read, observed, or quantitated on the test device. Depending on the particular test, the device may contain a built-in acidifying agent or a filtering material, and assay components deposited in strips, zones or other regions of defined dimensions. Those components that must be kept separate until the sample is added are isolated by gaps or barriers that provide the spatial separation. In many cases, some of the assay components will be affixed to the inner surface of the device by binding matrices that are insoluble in the sample liquid while others are soluble and readily dispersible in the sample liquid upon contact to travel with the sample through the device.

As noted above, assays in accordance with this invention can be performed with swabs and other transfer implements that pick up the assay components and permit the user to read the assay result directly on the implement. Transfer implements can be used with both types of substrates described above, i.e., those whose reporter groups are chromogens or other species that undergo a detectable change as a direct result of their release from the substrate residue, and those whose reporter groups are reagents that produce a detectable change in a separate indicator. When reporter groups that produce a change in a separate indicator are used, the implement can first be applied to the substrate and then to the indicator. In some cases, a proper result can be achieved by contacting the indicator within thirty seconds of contacting the substrate. In others, best results will be achieved when there is more of a time delay between these two contacts to allow the enzyme time to act upon the substrate and to avoid or minimize any inhibitory effect the indicator may have on the enzyme. In these cases, preferred time delays are at least two minutes, and most preferably from about five minutes to about thirty minutes.

In test devices where the solid-phase reagents reside in films on the inner surface of the device, these films may be formed by applying the reagents in liquid form followed by drying or other solidification. The liquid form of the reagent can for example be a solution or suspension of the reagent, or an uncured liquid form of a support matrix in which the reagent will be retained. The solidification step can thus be an evaporation of the solvent or suspending liquid or a curing of the matrix precursor. Additional materials may be included in the film for a variety of purposes, such as for example:

(1) to facilitate the application of the liquid to the surface by modifying the viscosity of the liquid,
(2) to help form a continuous smooth solid layer that remains uniform and does not disintegrate or granulate over time or upon the application of additional layers over the initial layer, or
(3) to modify the solubility of the layer with solvents used in layers to be applied over the layer or to make the layer soluble in solvents which do not dissolve layers applied underneath; or combinations of these purposes. Polymeric materials can be used for one or all of these purposes. Celluloses and various cellulosic derivatives are particularly useful, the derivatives substituted appropriately to achieve the desired solubility characteristics.

The reagent films in these test devices may also include additives that enhance stability and shelf-life as well as additives that facilitate dissolution of the substrate, the catalytically active hydrolase, or other components that function best when in solution. Examples of additives that improve the stability of the reagents are buffers; antioxidants such as butylated hydroxytoluene (BHT), butylated hydroxyanisole (BHA), ascorbate, and dithiothreitol (DTT); as well as metal binding components and chelators such as ethylenediaminetetraacetic acid (EDTA) and ethylene glycol-bis($\beta$-aminoethyl ether) (EGTA). Examples of additives that facilitate the dissolution, solubilization, or dispersion of the various components are mannitol, sorbitol, polyethylene glycol, lactose, and mild detergents. Detergents or other lysing agents can also be included for purposes of lysing the trichomonads to release internal hydrolases from the trichomonads into the liquid.

In addition to the zones of assay components described above, preferred test devices of this invention include a built-in positive control, and further preferred devices include both a built-in positive control and a built-in negative control. The positive control is defined as a substance or region on the device that causes the device to emit the same detectable signal that would be caused by application of an actual specimen that displays the target hydrolase activity, or a similar detectable signal, except that the positive control produces the signal upon the application of any specimen or substitute fluid regardless of whether or not the specimen or substitute fluid displays such activity. The positive control thus indicates to the user that the detectable signal itself is functioning properly and is capable of being generated, thereby assuring that false negative readings will not occur when actual specimens are applied. A preferred positive control is one that is formed by an additional reagent zone located on the device separately from the actual test (substrate and indicator) zones. This positive control can consist of any chemical that would react with the indicator to produce a detectable response, such as one of the reporter groups incorporated in peptide substrates described above, or an analog of the reporter group. A preferred positive control material is sodium aminonaphthoate, which reacts with an indicator to produce a detectable response much as the reporter groups listed above, but possesses superior stability and extended shelf-life.

A negative control is a control that indicates to the user that the test device will not produce a signal when the applied sample is devoid of the target hydrolase activity. The negative control thereby assures the user that the device will not produce false positive results when an actual specimen is applied. The negative control can be activated by the same bodily fluid on which the test for the target hydrolase activity is performed or by a separate specimen of the fluid than the specimen used for the test, or by a substitute fluid such as the diluent used with the test specimen. One type of negative control is a zone that contains the same indicator as in the indicator test zone, but is located on the device at a location separate from the substrate zone, indicator test zone, and the positive control zone. When a specimen is applied to this negative control zone without having first been applied to the substrate, the zone is checked to see whether a change is observed in the indicator that is located in that zone. Such a change would indicate that the specimen contains an interferent, other than the target hydrolase activity, that directly causes the change in the indicator. One example of such an interferent is resorcinol that is present in some vaginal products and that by itself produces a color change in diazonium salts. Another type of negative control is one that includes both the indicator and an inhibitor of the target hydrolase. When a specimen is first applied to the substrate and then to this negative control zone, any color formation or other signal generation in this the negative control zone would then indicate the presence of an interferent in the specimen that causes the change in the indicator and is not affected by the inhibitor, i.e., an interferent other than the target hydrolase that causes the indicator to change.

According to one method of performing a negative control test in which the detectable signal is read on the transfer implement itself, the user places one or two drops of diluent on either the negative control reagent zone or on a clean implement, and then rubs the implement on the negative control zone. If no detectable response is seen on the implement, the negative control test indicates that no false positive results will occur when an actual specimen is applied to the test zone. If the implement develops a detectable response, the negative control test indicates that there is a risk of a false positive result when an actual specimen is applied to the test zone. After performing a successful negative control test, the user can then rub the same implement on the positive control zone to perform the positive control test. If the implement then fails to produce a detectable response, the positive control test would be interpreted as failed, i.e., there is a risk of false negative results when test specimens are applied. If however the implement develops a detectable response in the positive control test, the positive control test has succeeded, indicating that false negative results will not occur because of device failure. The positive and negative control tests are designed primarily to check the condition of the indicator, which in many cases will be the least stable reagent in this type of test device. These control tests can also be used to detect the presence of interferents in a specimen.

An alternative positive control test is one that tests the condition of the indicator while also testing for interfering substances in the test specimen. This control test can be performed using the implement containing the actual specimen to be tested for trichomonal hydrolase activity, rather than a separate implement. First, the diagnostic test for trichomonal hydrolase activity is performed. If the diagnostic test result is positive, there is no need for a positive control test, since the diagnostic test itself will have established that the indicator is functional. If the diagnostic test result is negative, the positive control test should be performed immediately afterward by rubbing the same specimen-containing implement on the positive control reagent zone. If a detectable response is produced at the positive control zone, the positive control test and hence the diagnostic test are interpreted as valid. If no detectable positive control response is produced, i.e., the result is negative rather than positive, the positive control is interpreted as failed, and the preceding diagnostic test would be considered invalid. A second fluid specimen from the same individual can also be used to perform the negative control to detect positive interference from the specimen itself If the negative control test produces no detectable signal, the negative control test and hence the actual diagnostic test are interpreted as valid. Alternatively, if the negative control test produces a detectable signal upon exposure to the fluid sample, i.e., the control test is positive instead of negative, the negative control is interpreted as failed and the preceding diagnostic test would be considered invalid.

A still further alternative for a positive control test is one that uses a control hydrolase in place of the sodium aminonaphthoic acid or other reagent that reacts directly with the indicator. This type of positive control tests the functionality of the substrate conjugate, indicator and reaction conditions. As with the positive controls described above, a control hydrolase resides in a separate zone, which the user rubs with an implement immediately after a negative test result is obtained from the diagnostic test. The results are then interpreted in the same way as in the preceding control test, but only after sufficient time has elapsed for the hydrolase to generate a positive result. The length of the additional waiting period depends on the nature and concentration of the hydrolase used. The hydrolase must be active on the substrate at the pH used in the device. Accordingly for a low pH test, a preferred hydrolase for the positive control zone is bromelain, an inexpensive thiol hydrolase that is stable in dry form and active at a low pH. Bromelain can be deposited in a dry film in a positive control reagent zone in sufficient quantity to provide a positive control result in less than two minutes.

To summarize, the functions that can be served by positive and negative controls are as follows:

(a) A positive control can provide assurance to the user that all test elements (the substrate conjugate, the indicator and the reaction conditions) are performing correctly, and can be relied upon to detect trichomonal or other target hydrolase activity in a specimen, if such activity is indeed present. A negative control can provide assurance that the test reagents can be relied upon not to generate a positive result in the absence of trichomonal or other target hydrolase activity. By performing these functions, the positive and negative controls serve as means for checking the quality of the reagents in the test device.

(b) A positive control can provide assurance that the specimen being tested does not contain interferents that can inhibit the trichomonal or other target hydrolases or, by other means, interfere with the ability of the trichomonal or other target hydrolases to generate a positive test result. Similarly, a negative control can provide assurance that the specimen being tested does not contain interferents that can generate a positive response in the absence of the hydrolase. By performing these functions, the positive and negative controls serve as means for checking the quality of the specimen itself.

(c) If a test device and its controls are designed and constructed such that the control elements of the device are the last portions of the test device to be contacted by the specimen either because of their location on the test device or because of the protocol for applying the specimen to the device, a properly functioning positive control provides an indication that the test device has been filled, or properly wetted, with the specimen. In serving this function, therefore, the positive control serves as a means to check the test procedure. Controls of this type are often termed "procedural controls." Checking the procedure is particularly important with clear or colorless specimens, in devices designed to contain small volumes, and in devices in which specimen flow paths are partially obstructed from view.

One example of a test device embodying some of the concepts of this invention is shown in FIG. 1. This device and others within the scope of this invention can be of any size and shape, but it is particularly convenient to use a device that is similar in size and shape to a common credit card. The view in FIG. 1 is a longitudinal vertical cross section with the device held horizontally with its operative surface facing upward, this being the position in which the device is most likely to be used.

The base of the device is a solid rigid sheet 11 of inert non-porous material to whose upper surface is affixed a strip 12 of cellulosic or similarly porous material. The strip 12 is affixed to the underlying sheet by adhesive or any method that provides securement of the strip. The porous strip has two reagent zones 13, 14 defined at discrete regions along its length, each reagent zone having been applied by pipetting, stenciling, painting, printing or spraying techniques or any other method of deposition. Also shown is a swab 15 that is first wetted with a specimen of vaginal fluid and then applied to the test device at one end of the porous strip 12 to transfer the specimen to the porous strip. As noted above, the specimen can be applied to the porous strip by any implement capable of transferring a specimen; a swab is but one example. Once the specimen is applied, the specimen travels the length of the porous strip (left to right in the view shown in these Figures) by capillary action through the strip.

The first reagent zone 13 encountered by the migrating specimen is one that contains an indicator, and in those tests that involve an inhibitor, both the indicator and inhibitor are present in the first reagent zone as a solid mixture. The second reagent zone 14 contains a substrate that is susceptible to trichomonal hydrolytic activity. The indicator, and the inhibitor when present, are preferably deposited in the first reagent zone 13 in a manner permitting them to disperse in the specimen as the specimen migrates past, the specimen thereby drawing the indicator and inhibitor with it such that all three travel together toward the second reagent zone 14. The substrate in the second reagent zone 14 is preferably a conjugate consisting of a binding member covalently bonded to a reagent that causes a detectable change in the indicator. In alternative but similar devices, the relative positions of the two reagent zones can be reversed.

Figure 2:
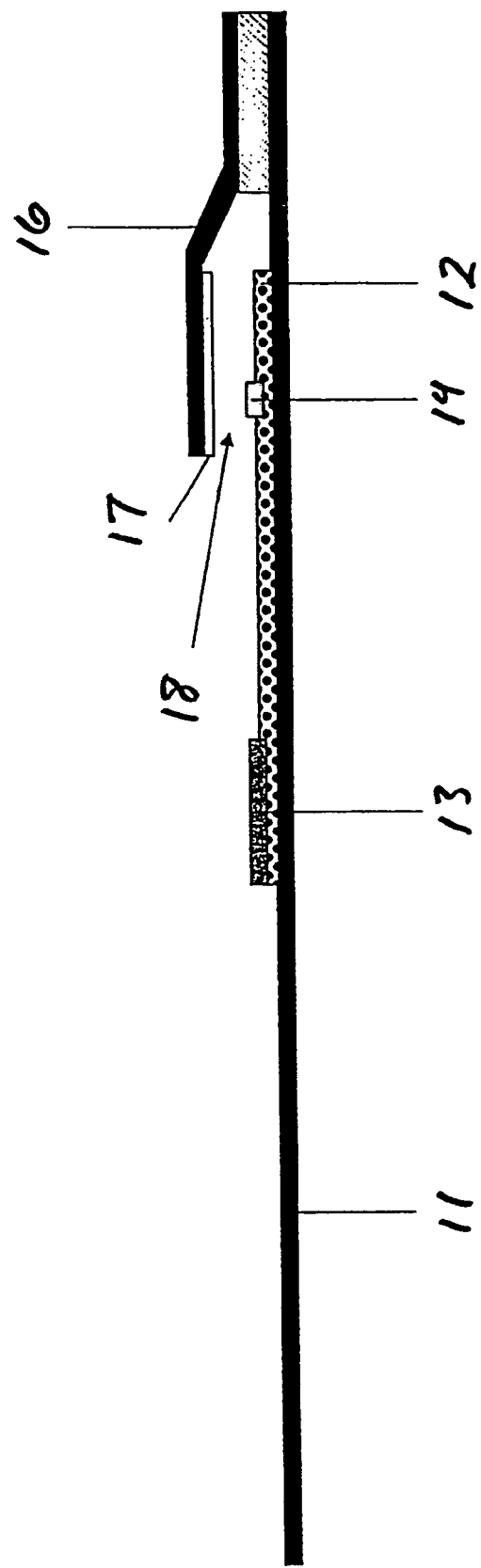
FIG. 2 is a vertical cross section of a second test device in accordance with this invention, representing a variation of the test device of FIG. 1.

The device of FIG. 2 is a variation of the device of FIG. 1, designed for applications where a separate development reagent is used for enhancing the detectability of the change in the indicator. The swab of FIG. 1, although not shown, is used to apply a specimen to this test device in the same manner as in FIG. 1, and the test devices are identical except that the test device of FIG. 2 contains a second sheet of solid non-porous inert support material 16 affixed to the first sheet by means of adhesive to form a flap that extends over the second reagent zone 14. On the side of the flap that faces the lower sheet is a layer of the development reagent 17 normally separated from the second reagent zone 14 by a gap 18. Once the specimen has reached the second reagent zone 14, the flap is pressed against the lower portion of the device to place the development reagent in contact with the second reagent zone. The flap is then lifted and the second reagent zone is observed to determine whether the detectable change has occurred.

Figure 3A:
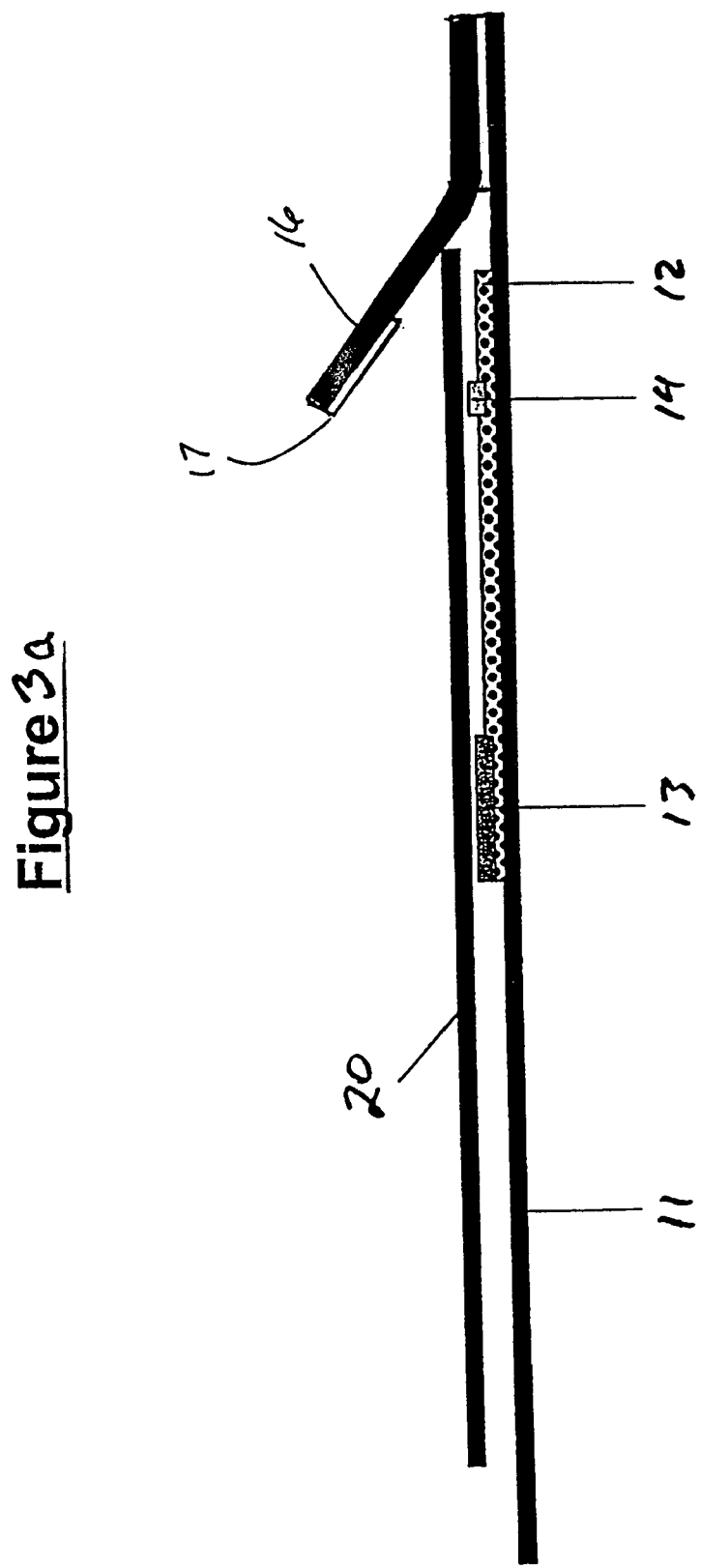
Figure 3D:
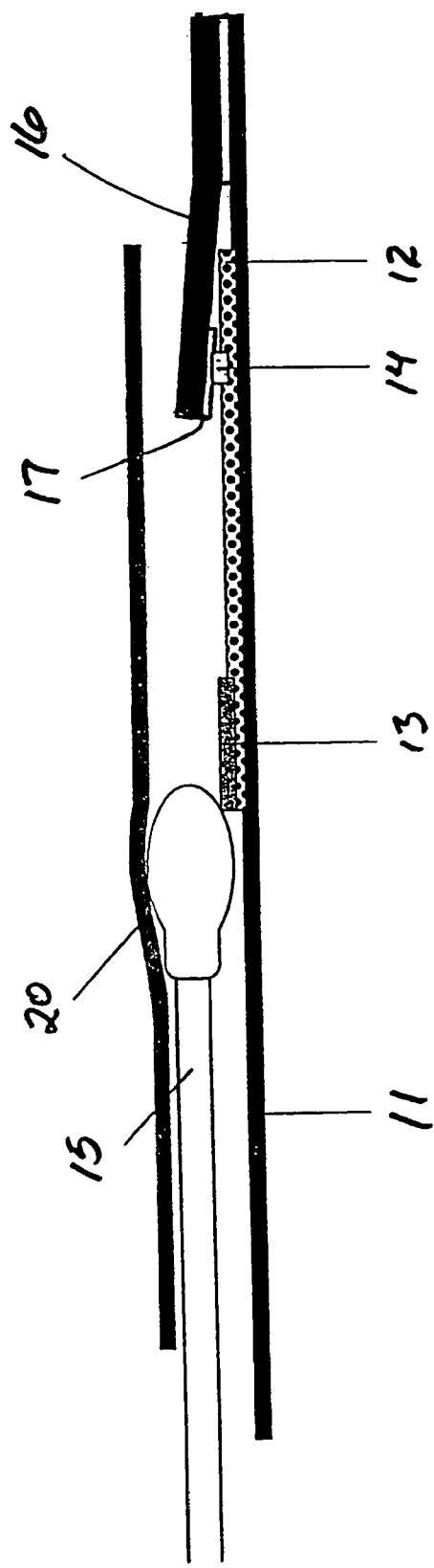

A further variation is the device shown in FIGS. 3a, 3b, 3c, and 3d. This device is similar to that of FIG. 2, except that the flap 16 is separated from the reagent zone 14 on the lower portion (or base sheet) of the device by an intermediate sheet or shield 20. This intermediate sheet 20 is at least partially transparent. Application of the specimen, as shown in FIG. 3b, is achieved by inserting a wetted swab (or other implement carrying the specimen) between the base sheet 11 and the intermediate sheet 20. The intermediate sheet 20 is bonded or otherwise secured to the base sheet 11 along the longitudinal edges of these sheets, which are not visible in these Figures since the Figures are longitudinal vertical cross sections. The left ends of the sheets are not bonded together but instead left open to form an opening for insertion of the swab 15, as shown in FIGS. 3b, 3c, and 3d. The swab is inserted deeply enough that its head comes into contact with the nearest end of the porous strip 12, and migration of the specimen proceeds as in the devices of the preceding Figures. After sufficient time has elapsed to allow the specimen to reach the second reagent zone 14 (which contains the substrate), the device is manually bent as shown in FIG. 3c, causing the flap 16 to separate from the base sheet 11 and the intermediate sheet 20, and due to the resiliency of the intermediate sheet 20 thereby causing the intermediate sheet 20 to lift off of (and out of contact with) the base sheet 11. The device is then allowed to resume its flat configuration (FIG. 3d), which may occur by simply releasing the manual pressure on the device provided that the device is sufficiently resilient. Upon resuming this configuration, the flap 16 comes into direct contact with the porous sheet 12, thereby bringing the development reagent 17 in contact with the indicator zone 14.

The various sheets shown in FIGS. 1, 2, and 3a through 3d are fabricated of solid material that is chemically inert to all of the specimens, reagents, diluents and other materials that contact these sheets during the assay, and the sheets are preferably semi-rigid with a resiliency that allows them to be distorted (for example as shown in FIG. 3c) but causes them to resume their shape when they are released from the distortion. The reagent zones can be formed by applying the reagents to specific areas on any of the sheets by conventional methods of deposition such as printing, bonding, or the application of foils, paper disks, or the like. Indicia can also be placed on the sheets in the same manner. The intermediate sheet 20 and the flap 16 can be transparent to permit viewing of the regions that show the test results, or the ability to observe the results can be achieved by strategically placed holes that are either stamped, punched, or cut out of non-transparent sheets. One or more of the sheets can be opaque, since the test results will in most cases be viewed from only one side of the device. When transparent materials are used, suitable examples are polyethylene terephthalates (such as, for example, MYLAR®). The porous strip 12 can be made of a cellulosic or synthetic material that is readily wetted by aqueous liquids, that possesses the desired wicking and particle retention properties, and does not strongly bind or adsorb proteins. Examples of suitable materials are Ahlstrom 237 Grade filter paper and Whatman Grand 44 filter paper. The reagent zones can be applied to the porous strip as dried deposits or coatings, in geometric or specially arranged patterns that avoid direct contact between the reagents in different zones until the strip is wetted.

The test devices that contain two or three sheets can be formed in a variety of ways. Preferred methods involve securing together or laminating sheets of polymeric material with adhesives or heat sealing. The laminated sheets can form a thin, flattened card, or one or more of the sheets can be pressure-formed to form an open pocket (3a through 3d) for ease of insertion of the swab. The pocket is simply a convenience means to hold the swab against the end of the porous strip. Alternative means are readily devised.

A still further type of test apparatus embodying the concepts of this invention is shown in FIG. 4. This apparatus consists of a single sheet 30 with distinct reagent zones 31, 32, 33, 34 on its surface, and a swab 35. This apparatus is used by simply wetting an implement (shown in the Figure as a swab 35) with the specimen, then rubbing the wetted implement over the various reagent zones in a preselected sequence, and finally reading the test result on the implement itself. In the arrangement shown in FIG. 4, the leftmost reagent zone 31 contains a substrate, and the reagent zone 32 to the right of the substrate zone contains an indicator, both the substrate and indicator as described above. Optionally, one or more inhibitors of non target hydrolases can be incorporated into reagent zone 31. Rubbing the wetted implement first over the substrate zone 31 will cause substrate (and inhibitor, if present) to adhere to the swab, and then rubbing the implement over the indicator zone 32 will cause the indicator to adhere to the implement as well. The time interval between rubbing the implement over the substrate zone and then over the indicator zone can be varied to meet the specific needs of different target hydrolases. As in the other test devices and in the general description above, if the specimen contains trichomonal or other target hydrolase activity, this activity will cause hydrolytic cleavage of the substrate which will in turn result in a visible change in the indicator that is adhering to, or has otherwise been picked up by, the implement. The remaining zones are a negative control zone 33 and a positive control zone 34, both of which are used by rubbing the implement (independently of the indicator and substrate conjugate zones and of each other) with a specimen-wetted implement (or an implement wetted with a fluid other than a specimen) and determining that no color change (or other detectable change) appears on the implement for the negative control and that a color change (or other detectable change) does appear for the positive control, both of which are independent of whether or not there is trichomonal hydrolase activity in the specimen.

The following examples are offered for purposes of illustration only. Amino acids are represented by their common three-letter or one-letter codes, and the following additional abbreviations are used:

CBZ or Z carbobenzoxy
BZ benzoyl
BOC tert-butoxycarbonyl
MNA 4-methoxy-2-naphthylamine
βNA β-naphthylamine
AMC 7-amido-4-methylcoumarin Preparation of Materials A. Trichomonal Hydrolases MATERIALS: *T. vaginalis* culture (ATCC 30001) and collection buffer consisting of 14 mM maltose, 6 mM L-cysteine and 10 mM HEPES in phosphate buffered saline, approximately pH 6.5.

PROCEDURE: Hydrolases secreted by live trichomonads were collected by washing trichomonads in late log-phase culture by centrifugation once in collection buffer, resuspending the trichomonads at $10^7$ organisms/mL in collection buffer, incubating four hours at 35° C., pelleting by centrifugation, and filtering through a 0.45 micron pore filter. Aliquots of the filtrate were placed in microfuge tubes and stored at −80° C. until use.

B. Concentrated Trichomonal Hydrolases

The materials and procedure were identical to those used in the preparation of trichomonal hydrolases, but with the organisms at ten times the density. Trichomonads in late log-phase culture were washed by centrifugation once in collection buffer, resuspended at $10^8$ organisms/mL in collection buffer, incubated 4-5 hours at 35° C., and pelleted by centrifugation. Aliquots of the supernatant were placed in microfuge tubes and stored at −80° C. until use.

C. Soluble Trichomonal Hydrolases from Lysed *T. vaginalis* Cells

MATERIALS: *T. vaginalis* culture (ATCC 30001) and wash buffer consisting of 14 mM maltose in phosphate buffered saline, approximately pH 6.5.

PROCEDURE: Hydrolases were collected from lysed trichomonads by washing the trichomonads in late log-phase culture by centrifugation once in chilled (4° C.) wash buffer, resuspending at $10^8$ organisms/mL in deionized water, holding for one hour at room temperature to allow the organisms to swell up, vortexing two minutes to lyse the organisms, and pelleting by centrifugation. Aliquots of the supernatant was then placed in microfuge tubes and stored at −80° C. until use.

D. Total (Soluble and Particulate) Trichomonal Hydrolases from Lysed *T. vaginalis* Cells Using the same materials as those of C above, a similar procedure was used, except that hydrolases were collected from a different isolate of *T. vaginalis*, and the whole lysate was used rather than only the supernatant. Trichomonads in late log-phase culture were washed by centrifugation once in chilled (4° C.) wash buffer, resuspended at $10^8$ organisms/mL in deionized water, held 3-4 hours at 4° C. to allow the organisms to swell up, and vortexed briefly to lyse the organisms, and aliquots of the suspension were placed in microfuge tubes and stored at −80° C. until use.

E. ZRRR-MNA Substrate Films

MATERIALS: CBZ-Arg-Arg-Arg-MNA triacetate (ZRRR-MNA), 200 mM L-cysteine hydrochloride in water, and 25% (w/w) hydroxypropylcellulose in ethanol.

PROCEDURE: A 400 mM ZRRR-MNA stock solution was made by dissolving ZRRR-MNA in ethanol. For a solution containing 200 mM ZRRR-MNA, 20 mM L-cysteine, and 5% hydroxypropylcellulose, a mixture was made of 100 μL 400 mM ZRRR-MNA, 20 μL 200 mM L-cysteine, 40 μL ethanol, and 40 μL hydroxypropylcellulose in ethanol. For solutions containing lower concentrations of ZRRR-MNA, the volume of ZRRR-MNA was decreased correspondingly, and the difference in volume made up by adding additional ethanol. Substrate films were made by pipetting 1 μL of the mixture over a circular area approximately ¼-inch (0.64 cm) in diameter on a sheet of Mylar, and drying under a stream of dry nitrogen. The dried films were stored in a container with desiccant until used.

F. VLR-MNA Substrate Films

MATERIALS: D-Val-Leu-Arg-MNA (VLR-MNA), 200 mM L-cysteine hydrochloride in water, and 25% (w/w) hydroxypropylcellulose in ethanol.

PROCEDURE: A 400 mM VLR-MNA stock solution was made by dissolving VLR-MNA in a mixture of 80% (v/v) ethanol and 20% (v/v) 3M hydrochloric acid. For a film made using a 200 mM VLR-MNA solution, a mixture was made of 100 μL 400 mM VLR-MNA, 20 μL 200 mM L-cysteine, 64 μL ethanol, and 16 μL hydroxypropylcellulose in ethanol. Substrate films were made by pipetting 1 μL of the mixture over a circular area approximately ¼-inch (0.64 cm) in diameter on a sheet of Mylar, and drying under a stream of dry nitrogen. The dried films were stored in a container with desiccant until used.

G. Indicator Films Containing Diazonium Dyes

MATERIALS: Fast Red RL or Fast Garnet GBC, 10% w/w ethylcellulose in methanol, and Meyer rod, rubber roller, or other device for applying a thin film of liquid onto a plastic sheet.

PROCEDURES: Fast Red RL or Fast Garnet was dissolved in dimethylformamide, diluted in methanol, and then mixed with an equal volume of 10% ethylcellulose to achieve a final solution containing 10% v/v dimethylformamide, 5% w/w ethylcellulose, and the desired concentration of diazonium dye (10 mM Fast Garnet or 64-100 mM Fast Red RL). The dye solution was applied to a Mylar sheet as a thin coating using a #10 Meyer rod, roller or other means, and subjected to a flow of warm air for rapid drying. The dried films were stored in a container with desiccant until used.

Experiment 1

This experiment examines the hydrolysis of the substrates CBZ-Arg-Arg-MNA (ZRR-MNA) and D-Val-Leu-Lys-MNA (VLK-MNA) by trichomonal hydrolases over the pH range 2.8 to 9.2 and examines the impact of vaginal fluid on hydrolase activity at each pH.

Materials 200 mM buffer solutions:

Glycyl-glycine (Gly-gly), pH 2.8

Sodium acetate, pH 5.1

2-(N-Morpholino)propane-sulfonic acid (MOPS), pH 7.0

N-2-Hydroxyethylpiperazine-N'-2-ethanesulfonic acid (HEPES), pH 7.5

Tris(hydroxymethyl)aminomethane (TRIS), pH 8.0

Sodium borate, pH 9.5

Pooled normal vaginal fluid supernatant (NVS), prepared as follows: vaginal fluid specimens collected on Dacron swabs from normal, uninfected women were centrifuged to extract the fluid from the swabs, and the pooled fluid was frozen until use. The thawed fluid was centrifuged to pellet the particulate matter, the particulate materials and the supernatant were separated and each was diluted 1:10 in acetate buffer.

2 mM CBZ-Arg-Arg-MNA acetate (ZRR-MNA), first prepared as a 100 mM solution in dimethylformamide, then diluted to 2 mM in deionized water 2 mM D-Val-Leu-Lys-MNA (VLK-MNA), first prepared as a 100 mM solution in dimethylformamide, then diluted to 2 mM in deionized water Indicator solution consisting of a freshly-made mixture of 100 μL of 25 mM para-dimethylamino cinnamaldehyde in ethanol, 900 μL of 10% w/v 2% sodium dodecyl sulfate, 1.35 mL of 100 mM citric acid, 450 μL of 200 mM disodium phosphate, and 3.5 mL water 100 mM acetic acid buffer, pH 3.7

Procedures

Assays without normal vaginal fluid supernatant present: Two sets of six wells in a microtiter plate were prepared, with each well containing 80 μL of one of the six 200 mM buffers, 10 μL of water and 10 μL of diluted trichomonal hydrolases. Ten μL of ZRR-MNA was added to each well in the first set of wells, and 10 μl of VLK-MNA was added to each well in the second set of wells. After fifteen minutes, 100 μl of indicator solution was added to each well. Because a high pH can reduce the intensity of color produced by the indicator solution, 50 μl of 100 mM acetic acid buffer, pH 3.7, was added to each well except the pH 2.8 wells (water was substituted for the acetic acid in those wells). After another fifteen minutes, the absorbance of the solutions in the wells was measured on a microtiter plate reader set on 540 nm wavelength.

Assays with normal vaginal fluid supernatant (NVS) present: The procedure of the preceding paragraph was followed, except that 10 μL of diluted NVS was added to the wells in place of the 10 μL of water.

Results

Assays without normal vaginal fluid supernatant present: The hydrolytic activity of the trichomonal enzymes, as reflected by the development of a pink or fuchsia color and increased absorbance at 540 nm, was high across a very broad pH range, as shown in Table 1.1 below. When ZRR-MNA was used as the substrate, the enzyme activity varied only slightly between pH 2.8 and pH 8.0 (absorbance readings ranged from 0.631 to 0.738), with a decrease observed only when the pH was 9.2 (absorbance dropped to 0.172). A different pH profile was observed when VLK-MNA was used as the substrate, with a peak of activity at pH 5.1 (absorbance of 1.622) and high activity at pH 9.2 (absorbance of 1.459). Across the entire pH range tested, a more intense color was produced with VLK-MNA compared to ZRR-MNA.

TABLE 1.1

Assays Without Vaginal Fluid Supernatant Present: Absorbance Readings at Different pH Levels

| | Buffer: | | | | | |
|---|---|---|---|---|---|---|
| | Gly-gly | Acetate | MOPS | HEPES | TRIS | Borate |
| | pH: | | | | | |
| Substrate | pH 2.8 | pH 5.1 | pH 7.0 | pH 7.5 | pH 8.0 | pH 9.2 |
| ZRR-MNA | 0.631 | 0.792 | 0.638 | 0.738 | 0.667 | 0.172 |
| VLK-MNA | 0.691 | 1.622 | 1.087 | 1.217 | 1.219 | 1.459 |

Assays with normal vaginal fluid supernatant (NVS) present: The presence of a small amount of vaginal fluid greatly reduced the hydrolytic activity of the trichomonal hydrolases, as shown in Table 1.2 below. Hydrolysis of ZRR-MNA in the presence of NVS was low at pH 2.8, 5.1, and 9.2 (absorbance readings of 0.082-0.089), and hydrolysis of VLK-MNA in the presence of NVS was low across the entire pH range tested (absorbance readings of 0.062-0.094). With ZRR-MNA as the substrate, enzyme activity was highest in pH 8 TRIS buffer (absorbance reading of 0.403); at this pH, the color production was 60% of that observed when vaginal fluid was not present (0.403/0.667).

TABLE 1.2

Assays With Vaginal Fluid Supernatant Present: Absorbance Readings at Different pH Levels

| | Buffer: | | | | | |
|---|---|---|---|---|---|---|
| | Gly-gly | Acetate | MOPS | HEPES | TRIS | Borate |
| | pH: | | | | | |
| Substrate | pH 2.8 | pH 5.1 | pH 7.0 | pH 7.5 | pH 8.0 | pH 9.2 |
| ZRR-MNA | 0.085 | 0.082 | 0.313 | 0.386 | 0.403 | 0.089 |
| VLK-MNA | 0.094 | 0.065 | 0.066 | 0.063 | 0.073 | 0.062 |

Interpretation

These results show that trichomonal hydrolases are active across a broad pH range, but that the optimum pH for maximum hydrolase activity varies with the substrate used. The optimum pH is also affected by the presence of vaginal fluid supernatant, which can be strongly inhibitory. For example, when vaginal fluid is not present in the assay mixture, the production of pink color from hydrolysis of ZRR-MNA by trichomonal enzymes is similar whether the pH is as low as 2.8 or as high as 8, but in the presence of vaginal fluid, color production is much less inhibited at pH 7 or 8 than at pH 2.8 or 5.1. The presence of vaginal fluid supernatant in the assay can strongly affect whether a specific substrate is readily hydrolyzed by trichomonal enzymes. This is especially true for VLK-MNA, which is readily hydrolyzed by trichomonal enzymes when no vaginal fluid is present, but poorly hydrolyzed in the presence of even a small amount of vaginal fluid. To produce a useful test system based on the activity of trichomonal hydrolases in the presence of vaginal fluid, it is important to define the best substrate and pH using either a mixture of trichomonal hydrolases and normal vaginal fluid supernatant prepared in the laboratory, or vaginal fluid specimens from subjects with trichomoniasis. For the initial selection of suitable substrates that are readily hydrolyzed by trichomonal hydrolases, vaginal fluid supernatant, rather than whole vaginal fluid, is preferred, since whole vaginal fluid contains non-trichomonal hydrolases associated with the particulate matter (as the experiments below will demonstrate).

Experiment 2

This experiment examines the hydrolysis of the substrates CBZ-Arg-Arg-MNA (ZRR-MNA), BOC-Leu-Arg-Arg-AMC (BLRR-AMC), BOC-Leu-Lys-Arg-AMC (BLKR-AMC), and CBZ-Lys-Lys-Arg-AMC (ZKKR-AMC) by trichomonal hydrolases and vaginal fluid hydrolases.

Materials

Buffer solutions consisting of 200 mM sodium acetate, pH 5, or 200 M Tris-(hydroxymethyl)aminomethane (TRIS), pH 8

100 mM CBZ-Arg-Arg-MNA acetate (ZRR-MNA), in ethanol 100 mM BOC-Leu-Arg-Arg-AMC (BLRR-AMC) in dimethylformamide 100 mM BOC-Leu-Lys-Arg-AMC (BLKR-AMC) in dimethylformamide 100 mM CBZ-Lys-Lys-Arg-MNA (ZKKR-AMC), in water 6.3 mM L-cysteine hydrochloride in water pooled normal vaginal fluid supernatant (NVS) prepared by collecting vaginal fluid specimens on Dacron swabs from normal, uninfected women, centrifuging to extract the undiluted fluid from the swabs and to pellet the particulate matter, and pooling the supernatants whole normal vaginal fluid (NVF) from a single normal, uninfected donor, prepared by centrifuging a Dacron swab containing a vaginal fluid specimen to extract the undiluted fluid from the swab, following by mixing to resuspend the particulate matter in the fluid 96-well microtiter plate with 200 µL microwells.

60-well microwell mini tray with 20 µL conical microwells.

indicator solution consisting of 0.4 mM para-dimethyl amino cinnamaldehyde, 1.4% (w/v) sodium dodecyl sulfate, and 100 mM citric acid (pH 4).

Procedure

Substrate solutions containing 8 mM of one of the four substrates (ZRR-MNA, BLRR-AMC, BLKR-AMC, ZKKR-AMC) in one of the two buffers (acetate, TRIS) were prepared by mixing 4 µL 100 mM substrate with 6 µL 6.3 mM L-cysteine, 14 µL 200 mM buffer and 26 µL water. Assays of trichomonal hydrolase activity, with or without the addition of NVS, were performed in 200 µL microwells. In one set of microwells, 10 µL of each substrate/buffer combination was mixed with 10 µL of undiluted trichomonal hydrolases. In a second set of microwells, 10 µL of each substrate/buffer combination was mixed with 10 µL of a mixture of 90% v/v trichomonal hydrolases and 10% NVS. Fifteen minutes later, 50 µL of indicator solution was added to each well. After another fifteen minutes, the absorbance of each solution in the wells was measured on a microtiter plate reader set on 540 nm wavelength.

Due to the partial opacity of cells and other particulate matter in whole vaginal fluid, assays of hydrolase activity present in whole vaginal fluid were performed in 20 µL conical microwells and scored visually. The vaginal fluid from a single normal, uninfected donor was agitated to resuspend the particulate matter, and 2 µL aliquots of the vaginal fluid were mixed with 2 µL of each substrate/buffer combination. To retard evaporation from the wells, water was pipetted into the mini-tray adjacent to the wells prior to replacing the tray cover. Fifteen minutes later, 2 µL of indicator solution was added to each well. After another fifteen minutes, the color in each well was visually scored in 0.5-unit increments using the 0-6 scale presented in Table 2.1.

TABLE 2.1

| Color Scale | |
|---|---|
| Color | Color Score |
| Yellow | 0 |
| Peach | 1 |
| Orange | 2 |
| Light to medium pink | 3 |
| Dark pink or red | 4 |
| Fuchsia | 5 |
| Purple | 6 |

Results

Hydrolase activity by trichomonal hydrolases was detected with all four of the peptide substrates tested, at both pH 5 (Table 2.2 below) and pH 8 (Table 2.3 below). At pH 5, all four substrates registered sharp decreases in activity when vaginal fluid was added. Inhibition of trichomonal hydrolases from vaginal fluid supernatant was greatest with ZRR-MNA, with a drop in absorbance from 0.420 to 0.068 at pH 5, and from 0.385 to 0.182 at pH 8. No inhibition of trichomonal hydrolases from vaginal fluid supernatant was observed with BLRR-AMC, BLKR-AMC, or ZKKR-AMC at pH 8. Considerable hydrolytic activity was detected in whole vaginal fluid (with the particulate matter included) using ZRR-MNA at pH 5, or any of the substrates at pH 8. However, BLRR-AMC, BLKR-AMC, and ZKKR-AMC had comparatively low sensitivity to the hydrolases present in whole normal vaginal fluid at pH 5.

TABLE 2.2

Hydrolase Assays at pH 5

| | Color Scores Substrate: | | | |
|---|---|---|---|---|
| | ZRR-MNA | BLRR-AMC | BLKR-AMC | ZKKR-AMC |
| Trichomonal hydrolases | 0.420 | 0.536 | 0.638 | 0.225 |
| Trichomonal hydrolases + NVS | 0.068 | 0.114 | 0.123 | 0.099 |
| Whole normal vaginal fluid | 3 | 0.5 | 0.5 | 0.5 |

TABLE 2.3

Hydrolase Assays at pH 8

| | Color Scores Substrate: | | | |
|---|---|---|---|---|
| | ZRR-MNA | BLRR-AMC | BLKR-AMC | ZKKR-AMC |
| Trichomonal hydrolases | 0.385 | 0.463 | 0.649 | 0.357 |
| Trichomonal hydrolases + NVS | 0.182 | 0.568 | 0.731 | 0.352 |
| Whole normal vaginal fluid | 4 | 6 | 6 | 2 |

Interpretation

While Experiment 1 demonstrated that trichomonal hydrolases could cleave peptide substrates that have a 4-methoxy-2-naphthylamide (MNA) reporter group attached to a Lysine or Arginine group-on a short peptide, and that hydrolysis could occur across a wide pH range, Experiment 2 demonstrates that trichomonal hydrolases can cleave peptide substrates that have a 7-amido-4-methylcoumarin (AMC) reporter group attached to a Lysine or Arginine group on a short peptide.

Experiment 3

This experiment demonstrates that most of the interfering hydrolytic activity present in vaginal fluid collected from normal, uninfected women is present in the particulate matter and can be largely removed by centrifugation.

Materials

Swabs (two per donor) containing vaginal fluid specimens collected from normal, uninfected women at intervals of 1-2 days apart Substrate solutions consisting of 8 mM CBZ-Arg-Arg-MNA acetate (ZRR-MNA), 0.8 mM L-cysteine, and either 100 mM sodium acetate, pH 5, or 100 mM Tris(hydroxymethyl)aminomethane (TRIS), pH 8

Indicator solution consisting of 0.4 mM para-dimethylamino cinnamaldehyde, 1.4% w/v sodium dodecyl sulfate, and 100 mM citric acid (pH 4)

Procedure

Pairs of vaginal fluid specimens were obtained from donors on three separate days—Day 1, Day 3, and Day 4—and tested on the day of collection. The vaginal fluid was extracted from each swab by centrifugation. The vaginal fluid supernatant from the first swab from each donor was used without resuspending the particulate matter that had formed a pellet in the bottom of the microfuge tubes during centrifugation. The vaginal fluid from the second swab from each donor was mixed vigorously to resuspend the particulate matter to form "whole" vaginal fluid. For each donor, 2 µL of vaginal fluid supernatant was mixed with 2 µL of pH 5 substrate solution, and 2 µL of vaginal fluid supernatant was mixed with 2 µL of pH 8 substrate solution on a sheet of parafilm. Likewise, for each donor, 2 µL of whole vaginal fluid was mixed with 2 µL of pH 5 substrate solution, and 2 µL of whole vaginal fluid was mixed with 2 µL of pH 8 substrate solution. The sheet of parafilm was placed into a humidified box to retard evaporation of the liquid drops. After fifteen minutes, 2 µL of indicator solution was added to each drop. Ten minutes later, the color of each drop was visually scored in 0.5 unit increments using the 0-6 scale presented in Table 2.1 above.

Results

The results for pH 5 and pH 8 are shown in Tables 3.1 and 3.2, respectively.

TABLE 3.1

Hydrolase Activity at pH 5 by Color Scale

| Sample | Day 1 | Day 3 | Day 4 |
|---|---|---|---|
| Donor A - whole vaginal fluid | 0 | 0 | 1 |
| Donor A - vaginal fluid supernatant | 0 | 0 | 0 |
| Donor B - whole vaginal fluid | 0 | 3 | 0 |
| Donor B - vaginal fluid supernatant | 0 | 0 | 0 |
| Donor C - whole vaginal fluid | 0 | 3 | 1 |
| Donor C - vaginal fluid supernatant | 0 | 0 | 0 |
| Donor D - whole vaginal fluid | 0 | 0.5 | 4 |
| Donor D - vaginal fluid supernatant | 0 | 0.5 | 1 |

TABLE 3.2

Hydrolase Activity at pH 8 by Color Scale

| | Day 1 | Day 3 | Day 4 |
|---|---|---|---|
| Donor A - whole vaginal fluid | 0 | 1 | 3 |
| Donor A - vaginal fluid supernatant | 0 | 0 | 0 |
| Donor B - whole vaginal fluid | 2.5 | 3 | 0 |
| Donor B - vaginal fluid supernatant | 0 | 0 | 0 |
| Donor C - whole vaginal fluid | 0 | 4 | 4 |
| Donor C - vaginal fluid supernatant | 0 | 1 | 4 |
| Donor D - whole vaginal fluid | 0 | 5 | 5 |
| Donor D - vaginal fluid supernatant | 0 | 0 | 0 |

The activity of interfering hydrolases present in the vaginal fluid of normal, uninfected women can vary considerably in unpredictable fashion from day to day. For example, at pH 5 hydrolytic activity in the whole vaginal fluid from Donor B was undetectable on Day 1, fairly high two days later (producing a score of 3), and then undetectable on the following day (Table 3.1). In general, the activity of hydrolases present in vaginal fluid was higher at pH 8 than pH 5 (compare Tables 3.1 and 3.2). In most cases, the hydrolytic activity was associated with the particulate matter in the vaginal fluid, and either absent or greatly decreased in the supernatant portion of the vaginal fluid. For example, the hydrolytic activity in whole vaginal fluid from Donor D, when measured at pH 8 on Days 3 and 4, was very high, yet undetectable in the supernatant (Table 3.2). In rare cases, hydrolytic activity was high in the supernatant also, such as with Donor C on Day 4 (Table 3.2). Some of the vaginal fluid particulate matter from this donor may have accidentally been resuspended during processing and therefore present in the supernatant.

Interpretation

These results show that much of the interfering hydrolytic activity present in the vaginal fluid of normal, uninfected women is associated with particulate matter in the vaginal fluid such as bacteria, vaginal cells, or other cellular debris. Removal of the particulate matter by centrifugation or other means greatly decreases the presence of non-trichomonal hydrolases in vaginal fluid specimens, thereby providing the assay with selectivity toward trichomonal hydrolase activity.

Experiment 4

This experiment offers further evidence that most of the interfering hydrolytic activity present in vaginal fluid collected from normal, uninfected women is present in the particulate matter. In this experiment, the particulate hydrolases are removed by filtration, specifically centrifugal filtration.

Materials

Swabs (two per donor) containing vaginal fluid specimens collected from normal, uninfected women Trichomonal hydrolases prepared as described in Preparation C above Diluent solution consisting of 50 mM Tris(hydroxymethyl)aminomethane (TRIS) buffer, pH 8.3, in a 20 mL dropper bottle Polystyrene 1.5 mL cuvettes Nanosep MF centrifugal filtration devices with 0.2 micron pores (Pall Filtron), each fitted with a disk of coarse filter paper inside the upper chamber to serve as a prefilter Substrate solution consisting of 4 mM CBZ-Arg-Arg-MNA acetate (ZRR-MNA) and 1 mM L-cysteine in a 2 mL dropper bottle Indicator solution consisting of 0.8 mM para-dimethylamino cinnamaldehyde and 2% w/v sodium dodecyl sulfate in a 2 mL dropper bottle 400 mM malic acid, pH 3.4, in a 2 mL dropper bottle Procedure To extract the vaginal fluid from each Dacron swab, ten drops (approximately 400 µL) of buffer were placed in a cuvette, then the swab was inserted into the cuvette and rotated several times. As the swab was rotated, the narrow portion of the tapered cuvette squeezed the swab head to thoroughly mix the contents of the swab into the diluent solution. The swab was removed and discarded. Both swabs from each donor were treated indentically up to this point, then 30 µL of trichomonal hydrolases was added to one of the cuvettes from each pair. Using disposable droppers, one drop of unfiltered fluid was transferred from each cuvette to separate microwells in a microtiter plate. The remaining fluid in each cuvette was poured into separate centrifugal filter devices. The filter devices were placed in a microfuge and centrifuged for five minutes. Using disposable droppers, one drop of filtrate was transferred from each filter device to separate microwells in the microtiter plate. One drop of substrate solution was added to each microwell, and the microtiter plate was gently tapped a few times to mix the contents of the wells. After ten minutes, one drop of indicator solution and one drop of malic acid was added to each well, and the microtiter plate was again gently tapped a few times to mix the contents of the wells. Five minutes later, the color in each well was visually scored in 0.5 unit increments using the 0-6 scale presented in Table 2.1 above.

Results

In this experiment, vaginal fluid from only two of the nine donors (Donors F and G) tested positive for hydrolase activity without supplementation with trichomonal hydrolases. Table 4.1 below shows that filtration completely removed the hydrolytic activity from these samples (compare the second and third columns of the table). When the vaginal fluid was supplemented with trichomonal hydrolases, all of the vaginal fluid specimens had high levels of hydrolase activity, with little difference between the unfiltered and filtered solutions (fourth and fifth columns of the table).

TABLE 4.1

Hydrolase Activity With and Without Filtration

| Specimens | Vaginal Fluid From Uninfected Subjects | | Vaginal Fluid Supplemented With Trichomonal Hydrolases | |
| --- | --- | --- | --- | --- |
| | Unfiltered | Filtered | Unfiltered | Filtered |
| Donor A | 0 | 0 | 4 | 4 |
| Donor B | 0 | 0 | 4 | 4 |
| Donor C | 0 | 0 | 4 | 4 |
| Donor D | 0 | 0 | 5 | 4 |
| Donor E | 0 | 0 | 4 | 4 |
| Donor F | 3.5 | 0 | 5 | 4 |
| Donor G | 0 | 0 | 4 | 4.5 |
| Donor H | 3.5 | 0 | 4 | 3.5 |
| Donor I | 0 | 0 | 5 | 5 |

Interpretation

There were fewer vaginal fluid specimens with detectable hydrolase activity in this Experiment than in Experiment 3, probably because of greater dilution of the vaginal fluid in this experiment. The interfering vaginal fluid hydrolases present in the two specimens with hydrolytic activity were decreased to undetectable levels by filtration, indicating that they are largely insoluble in water. When trichomonal hydrolases were added to the extracted vaginal fluid specimens, the trichomonal hydrolases passed through the filters readily, resulting in little difference between the filtered and unfiltered solutions, suggesting that these trichomonal hydrolases are soluble in water. As for many experiments described, the trichomonal hydrolases were added to vaginal fluid rather than tested alone, to insure that only hydrolases that are active in the presence of vaginal fluid were being detected.

Experiment 5

This experiment offers still further evidence that most of the interfering hydrolytic activity present in vaginal fluid collected from normal, uninfected women is present in the particulate matter. In this experiment, the particulate matter is removed by filtration which is achieved causing the specimens to flow longitudinally through a strip of porous material.

Materials

Trichomonal hydrolases prepared as described in Preparation B above

Porous material: SMW50 fiber, Manniweb Filtration Systems Products

Plastic drinking straw, cut 2 inches long and heat-sealed shut at one end

Buffer consisting of 100 mM imidazole solution, pH 7.3

Dacron swabs containing vaginal fluid specimens collected from a normal, uninfected woman Substrate solution consisting of 4 mM CBZ-Arg-Arg-MNA acetate (ZRR-MNA) in 100 mM imidazole, pH 7.3

Color developer solution made of a fresh mixture of equal volumes of the following indicator solution and acid solution:
  a. Indicator solution: 160 µL of 25 mM para-dimethylamino cinnamaldehyde in ethanol, 1 mL of 10% w/v sodium dodecyl sulfate, and 8.8 mL water
  b. 1 M malic acid, pH 3

Procedure

Three strips, 3 mm wide and 45-50 mm long, were cut from the porous material. Each strip was placed on a sheet of parafilm, and two 3 mm-wide bands of tape were affixed transversely across each strip. The first band of tape was placed 5 mm from the end of the strip and the second band of tape was placed 5 mm from the first band, dividing each strip into three sections, i.e., an upstream section at the starting end 5 mm in length, a middle section 5 mm in length, and a downstream section approximately 30-35 mm in length. Vaginal fluid specimens from the same donor were processed three different ways:

1. Extracted whole vaginal fluid: To extract the vaginal fluid from a Dacron swab head, 250 µL of buffer was pipetted into a heat-sealed straw and the swab was inserted into the straw. The swab was rotated inside the straw while pressure was applied to the sides of the straw to thoroughly mix the swab contents into the buffer. The swab was removed from the straw slowly while the sides of the straw were squeezed to express most of the liquid from the swab head.

Twenty-five µL of the extracted vaginal fluid was slowly pipetted onto a 45 mm long porous strip, in the middle section between the two strips of tape. After the extracted vaginal fluid had been completely absorbed into the strip, 50 µL of buffer was applied dropwise onto the upstream section of the strip (at the starting end), allowing the buffer to be absorbed into the strip between drops. After all of the liquid had been absorbed into the material and the entire strip was visibly wetted, the downstream section of the strip was cut transversely into small slices 3-5 mm long. Each slice, in sequence, was transferred to separate microwells in a 96-well microtiter plate, and then covered with 25 µL of substrate solution. After ten minutes, 25 µL of color developer solution was pipetted into each microwell. Five minutes later, the color that developed in each well was visually scored in 0.5 unit increments using the 0-6 scale presented in Table 2.1 above.

2. Blotted whole vaginal fluid: Instead of extracting the vaginal fluid using a straw, a swab containing a vaginal fluid specimen from the same donor was pressed several times onto the middle section of another 45 mm long porous strip. The swab head was blotted onto the strip until the material was flattened and visibly wetted with vaginal fluid. Fifty µL of buffer was pipetted dropwise onto the upstream section of the strip and the strip was processed as above.

3. Blotted whole vaginal fluid plus trichomonal hydrolases: To demonstrate mobility of trichomonal hydrolases through a porous strip, 4 µL of trichomonal hydrolases were pipetted onto the middle section of a 50 mm long strip (a longer strip was used to accommodate the additional 4 µl of fluid) after a swab as described in Part 2 was blotted onto the same section. Fifty µL of buffer was pipetted dropwise onto the upstream section of the strip and the strip was processed as above.

Results

The results are shown in Table 5.1 below where Section A is the upstream section, Section B the middle section, and Sections C2 through C8 the eight subsections of the longer downstream section.

TABLE 5.1

Hydrolase Activity Using Filter Strip

| | Strip Section: | | | | | | | | |
|---|---|---|---|---|---|---|---|---|---|
| | A | B | C1 | C2 | C3 | C4 | C5 | C6 | C7 | C8 |
| Extracted Vaginal Fluid | 0 | 3 | 0 | 0 | 0 | 0 | 0.5 | 0.5 | — | — |
| Blotted Vaginal Fluid | 0 | 3 | 0 | 0 | 0 | 0 | 0.5 | 0.5 | — | — |
| Blotted Vaginal Fluid Plus Trichomonal Hydrolases | 0 | 2.5 | 0 | 0 | 0 | 0 | 0.5 | 2 | 3 | 4 |

These results show that for the extracted vaginal fluid specimens, as expected, no hydrolytic activity was detected in the upstream section where the buffer was applied to the porous strip. Considerable hydrolytic activity was detected in the middle section, which was where the vaginal fluid was applied. No activity was detected in the first four slices cut from the downstream section of the strip closest to the middle section (subsections C1-C4), and low levels of hydrolytic activity were detected in the remaining two slices cut from the downstream section. The results for the blotted vaginal fluid were identical to those for the extracted vaginal fluid. The results from vaginal fluid supplemented with trichomonal hydrolases were similar for Sections A and B and the first four subsections of Section C. Unlike the other strips, however, there was considerable hydrolytic activity in the slices cut from the distal end of Section C (subsections C6-C8), noting once again that this strip contained two more subsections because of its greater length.

Interpretation

Most of the hydrolytic activity present in whole normal vaginal fluid was detected on the porous strip where the vaginal fluid was applied, in Section B. The lateral flow of buffer from the section at the starting end through the middle section to the downstream section did not cause much of the hydrolytic activity to flow with the buffer. This is strong evidence that most of the vaginal fluid hydrolases being detected by this assay are bound to or otherwise associated with particulate matter that is trapped in or on the porous material. A very small portion of the vaginal fluid hydrolases are apparently in a soluble form. Those that were soluble were carried along by the flow of buffer to the end of the strip. The two methods of transferring the vaginal fluid from the swab to the paper strip had no effect on the amount of hydrolases trapped by the strip.

When trichomonal hydrolases were added to the vaginal fluid applied to a strip, there was no increase in activity detected in the middle section where these supplemented specimens were added, but there was a large increase in hydrolase activity at the very end of the strip. This indicates that trichomonal hydrolases are soluble and can readily migrate laterally through a porous strip by a flow of liquid in the strip. This observation indicates that test devices containing a porous strip to which a vaginal fluid specimen is transferred and which is then washed laterally with a buffer are selective for trichomonal hydrolases. The trichomonal hydrolases, but little of the vaginal fluid (particulate) hydrolases, will reach the end of the strip. By placing the substrate at the end of the strip, hydrolysis of the substrate would occur only if trichomonal (soluble) hydrolases are present in the specimen.

Experiment 6

This experiment demonstrates that certain protease inhibitors provide further selectivity to an assay for trichomonal hydrolase activity. The inhibitors used in this experiment were antipain (an inhibitor of thiol proteases) and chymostatin (an inhibitor of chymotrypsin, a serine protease). Although these inhibitors can provide a certain degree of selectivity to assays performed on whole vaginal fluid specimens, they are particularly useful on vaginal fluid specimens from which the particulate hydrolases have been removed by filtration or centrifugation. A relatively low concentration of inhibitor is sufficient to eliminate the small amounts of soluble hydrolases that are variably present in some normal vaginal fluid specimens, and at the concentrations employed in this experiment, the inhibitors did not substantially inhibit the activity of the trichomonal hydrolases.

Materials

Swabs (two per donor) containing vaginal fluid specimens collected from normal, uninfected women Trichomonal hydrolases prepared as described in Preparation B Diluent consisting of 10 mM Lcysteine in water 0.5 mL centrifuge filter units with 0.2 micron-pore filter membranes 60-well microwell mini tray with 20 µL conical microwells (originally designed for serotyping)

100 mM CBZ-Arg-Arg-MNA acetate (ZRR-MNA) in ethanol

1M N-2-hydroxyethylpiperazine-N'-2-ethanesulfonic acid (HEPES), pH 7.6

200 µg/mL antipain in water 10 mM chymostatin, prepared by adding deionized water to a 330 mM stock made in DMSO Color developer solution made of a fresh mixture of equal volumes of the following solutions:
  a. Indicator solution: 320 µL of 25 mM para-dimethylamino cinnamaldehyde in ethanol, 1 mL of 10% w/v sodium dodecyl sulfate, and 7.7 mL water
  b. 400 mM malic acid, pH 3.4

Procedure

1. Demonstration of Strong Inhibition of Non-Trichomonal Hydrolases Present in Normal Vaginal Fluid Supernatants:

Substrate/inhibitor combinations were prepared by mixing 4 µL of 100 mM ZRR-MNA, 20 µL of 1M HEPES buffer, 56 µL of deionized water, and 20 µL of either antipain, chymostatin, or deionized water. Filtered vaginal fluid was prepared from each specimen as follows: the swab was placed in a cuvette containing 200 µL of diluent and the swab was rotated in the diluent to thoroughly mix the swab contents into the diluent. The swab was removed, the swab head was broken off into a microfuge tube, and the liquid remaining in the swab head was forced out by centrifugation. The fluid extracted from the swab was combined with the liquid in the cuvette, and the total volume of fluid was filtered using a centrifuge filter unit to remove particulate matter.

For each specimen, 4 µL of vaginal fluid filtrate was mixed with 4 µL of each of the three substrate/inhibitor combinations in separate microwells; one well contained 20 µg/mL antipain, one contained 1 mM chymostatin, and one bad no inhibitor. After ten minutes, 4 µL of color developer solution was added to each well. Ten minutes later, the color in each well was visually scored in 0.5 unit increments using the 0-6 scale presented in Table 2.1 above.

2. Demonstration of Weak Inhibition of Trichomonal Hydrolases:

Trichomonal hydrolases were added to each of the filtered vaginal fluid specimens—10 µL of trichomonal hydrolase preparation added to 90 µL vaginal fluid filtrate—and the above experiment was repeated.

Results

The results for the vaginal fluid supernatants from normal, uninfected women are shown in Table 6.1 and the results for the vaginal supernatants that had been supplemented with trichomonal hydrolases are shown in Table 6.2:

TABLE 6.1

Hydrolase Activity for Specimens from Uninfected Subjects With and Without Inhibitors

| | Inhibitor: | | |
|---|---|---|---|
| | None | Antipain | Chymostatin |
| Donor A | 2 | 0 | 0 |
| Donor B | 0 | 0 | 0 |
| Donor C | 2 | 0 | 0 |
| Donor D | 4 | 0 | 2 |
| Donor E | 2 | 0 | 0 |
| Donor F | 2 | 0 | 0 |

TABLE 6.2

Hydrolase Activity for Specimens Supplemented with Trichomonal Hydrolases With and Without Inhibitors

| | Inhibitor: | | |
|---|---|---|---|
| | None | Antipain | Chymostatin |
| Donor A | 4 | 4 | 3.5 |
| Donor B | 4 | 3.5 | 3.5 |
| Donor C | 4 | 3.5 | 3.5 |
| Donor D | 4.5 | 4 | 4 |
| Donor E | 3 | 3 | 3 |
| Donor F | 3 | 2.5 | 3 |

1. Demonstration of Strong Inhibition of Hydrolases Present in Vaginal Fluid Supernatants (Table 6.1)

The results in Table 6.1 show that five of the six normal vaginal fluid specimens contained hydrolases capable of hydrolyzing ZRR-MNA (second column of the table). Antipain completely inhibited the hydrolases in all five of these specimens (third column). Chymostatin completely inhibited the hydrolases in four of the five specimens, and partially inhibited the specimen with the highest enzyme activity (fourth column).

2. Demonstration of Weak Inhibition of Trichomonal Hydrolases (Table 6.2)

The results in Table 6.2 show that specimens demonstrated increased hydrolytic activity when augmented with trichomonal hydrolases (second column). Neither antipain nor chymostatin decreased the intensity produced by the trichomonal hydrolases by more than a half-unit score (third and fourth columns) compared to the wells that did not contain an inhibitor (second column).

Interpretation

This experiment clearly demonstrates that hydrolase inhibitors at appropriate concentrations selectively inhibit interfering hydrolases naturally present in normal vaginal fluid specimens while permitting trichomonal hydrolases to remain active. This offers a further improvement of the specificity of detection of trichomonal hydrolases. The inhibitors used in this experiment were of two distinct classes: antipain is a thiol protease inhibitor and chymostatin is an inhibitor of chymotrypsin, a serine protease. Each one however provided selective inhibition of interfering hydrolases.

Experiment 7

This experiment compares the selective inhibition of water soluble, non-trichomonal hydrolases by two thiol protease inhibitors, E64 and antipain, in vaginal fluid specimens collected from women attending an STD (sexually transmitted disease) clinic.

Materials

Swabs (two per donor) containing vaginal fluid specimens collected from women attending an STD clinic, many of whom had bacterial vaginosis, vaginal yeast infections, or other forms of vaginitis, and who were determined to be trichomonas-positive (vaginally infected with *T. vaginalis*) or trichomonas-negative by five-day culture for *T. vaginalis*

Plastic drilling straws, cut to 2-inch lengths and heat-sealed closed at one end 0.5 mL centrifuge filter units with 0.2 micron-pore filter membranes 96-well microwell plates with 250 µL round-bottom wells Substrate reagent solutions containing 4 mM CBZ-Arg-Arg-MNA acetate (ZRR-MNA), 400 mM imidazole buffer, pH 7.3, and one of the following two inhibitors:

0.4 mM trans-epoxysuccinyl-L-leucylamido-(4-guanidino) butane (E64) 5 µg/mL antipain Color developer solution made of a fresh mixture of equal volumes of the following solutions:

a. Indicator solution: 160 µL of 25 mM para-dimethylamino cinnamaldehyde in ethanol, 2 mL of 10% w/v sodium dodecyl sulfate, and 7.8 mL water b. 400 mM malic acid, pH 3.4

Procedure

Each vaginal fluid specimen from a clinic patient was placed inside a heat-sealed plastic straw containing 250 µL of deionized water. The swab was rotated while the straw was being pinched, to thoroughly mix the swab contents into the water, then the swab was removed while the straw was being squeezed to express most of the liquid from the swab tip. To remove particulate matter, the extracted vaginal fluid was transferred to a filter unit and centrifuged for up to five minutes in a small portable centrifuge. Twenty-five µL of the substrate solution containing E64 was pipeted into a round-bottom microwell, and 25 µL of the substrate solution containing antipain was pipeted into a second well. Twenty-five µL of the filtered vaginal fluid was added to each of two wells. After ten minutes, 25 µL of color developer solution was added to each well. Five minutes later, the color in each well was visually scored in 0.5 unit increments using the 0-6 scale presented in Table 2.1.

Results

The results are shown in Table 7.1:

TABLE 7.1

Hydrolase Activity in Specimens from Trichomonas-Positive and Trichomonas-Negative Subjects With Inhibitors
Color Score

| | Inhibitor: | |
|---|---|---|
| | E64 | Antipain |
| Trichomonas-positive (n = 5): | | |
| 0 | 2 | 2 |
| 1-1.5 | 0 | 0 |
| 2-2.5 | 1 | 1 |
| 3-3.5 | 0 | 0 |
| 4-4.5 | 2 | 2 |
| 5-6 | 0 | 0 |
| Trichomonas-negative (n = 21): | | |
| 0 | 21 | 17 |
| 1-1.5 | 0 | 2 |
| 2-2.5 | 0 | 2 |
| 3-3.5 | 0 | 0 |
| 4-4.5 | 0 | 0 |
| 5-6 | 0 | 0 |

Three of five specimens that were culture-positive for trichomonas produced a pink color in the test wells (upper half of Table 7.1). For these specimens, the choice of inhibitor did not affect the color scores; i.e., the wells containing E64 scored nearly the same (within a half-unit) as the matching wells containing antipain. The two culture-positive specimens that failed to produce a pink color had low numbers of parasites: only a few trichomonads were seen in the microscopic wet mount examination from one, and none were seen in the wet mount from the other specimen. All twenty-one culture-negative specimens scored zero in the wells containing E64, and eighteen of the twenty-one culture-negative specimens scored zero in the wells containing antipain (lower half of Table 7.1).

Interpretation

This experiment was designed to compare the efficacy of two inhibitors. Only two specimens were available from each donor at this clinic, so it was not possible to compare the two inhibitors while also testing the hydrolase activity in the absence of an inhibitor. As demonstrated in Experiment 6, however, a certain amount of non-trichomonal hydrolase activity may remain in vaginal fluid specimens after filtration, and antipain can be used to selectively inhibit this non-trichomonal hydrolase activity. Experiment 7 establishes that a different thiol hydrolase inhibitor, E64, also can be very effective at selectively inhibiting non-trichomonal hydrolases that may be present in vaginal fluid specimens. At the concentrations of inhibitor tested, E64 was more effective that antipain at selectively inhibiting non-trichomonal hydrolases present in vaginal specimens from clinic patients with non-trichomonal vaginal infections, while permitting trichomonal hydrolases to remain active.

Experiment 8

This experiment shows that certain polypeptides can be used to selectively inhibit non-trichomonal hydrolases present in vaginal fluid, with relatively little inhibition of trichomonal hydrolases while other polypeptides do not have these effects.

Materials

Swabs containing vaginal fluid specimens collected from four normal, uninfected women Trichomonal hydrolases prepared as described in Preparation A 60-Well microwell mini-tray with 20 µL conical microwells Substrate/polypeptide solutions containing 8 mM CBZ-Arg-Arg-MNA acetate (ZRR-MNA), 0.8 mM L-cysteine, 56 mM acetate (pH 5) or TRIS (pH 8) buffer, and 10 mM of one of the following polypeptides:

Lys-Arg-Gln-His-Pro-Gly (KRQHPG)
Lys-Pro-Gln-Leu-Trp-Pro (KPQLWP)
Arg-Lys-Asn-Val-Tyr (RKNVY)
Arg-Pro-Lys-Pro-Gln-Phe-Phe-Gly-Leu-Met (RPK-PQFFGLM)
No polypeptide (control)

Indicator solution consisting of 0.4 mM para-dimethylamino cinnamaldehyde, 1.4% w/v sodium dodecyl sulfate, and 100 mM citric acid (pH 4)

Procedure

The vaginal fluid was extracted from each swab by centrifugation, and then mixed to resuspend the particulate matter. For each donor, 2 µL of vaginal fluid was pipetted into each of ten microwells, then 2 µL of one of the ten substrate/buffer/polypeptide combinations was added to each well. Additionally, 2 µL of trichomonal hydrolases was mixed with 2 µL of each of the substrate/polypeptide combinations in set of ten wells. After fifteen minutes, 2 µL of indicator solution was added to each well. Ten minutes later, the color in each well was visually scored in 0.5 unit increments using the 0-6 scale presented in Table 2.1.

Results

The results for the tests at pH 5 are shown in Table 8.1 and those for the tests at pH 8 are shown in Table 8.2:

TABLE 8.1

Hydrolase Activity in Specimens from Uninfected Women Using Different Peptide Inhibitors at pH 5

| | Donor A | Donor B | Donor C | Donor D | Trichomonal Hydrolases |
|---|---|---|---|---|---|
| No polypeptide | 3 | 3 | 0 | 3 | 3 |
| KPQLWP | 0 | 0 | 0 | 0 | 3 |
| RKNVY | 0.5 | 0 | 0 | 0 | 3 |
| KRQHPG | 2 | 2 | 0 | 2 | 3 |
| RPKPQFFGLM | 0.5 | 1 | 0 | 0.5 | 1 |

TABLE 8.2

Hydrolase Activity in Specimens from Uninfected Women Using Different Peptide Inhibitors at pH 8

| | Donor A | Donor B | Donor C | Donor D | Trichomonal Hydrolases |
|---|---|---|---|---|---|
| No polypeptide | 3 | 3 | 2.5 | 3 | 3 |
| KPQLWP | 0.5 | 0.5 | 0 | 0 | 3 |
| RKNVY | 0.5 | 0.5 | 1 | 1 | 3 |
| KRQHPG | 2.5 | 2 | 0.5 | 2 | 3 |
| RPKPQFFGLM | 0.5 | 0.5 | 0 | 0 | 0.5 |

These tables show that when the assays were run at pH 5, the vaginal fluid from three of the four donors contained sufficient hydrolytic activity to produce color scores of 3 (the "No polypeptide" row in Table 8.1). The trichomonal hydrolases also produced a score of 3 in this assay. In presence of either KPQLWP or RKNVY, the vaginal fluid hydrolases produced very little color, with all but one well scoring zero, while the trichomonal hydrolases remained unaffected. When the assays were run at pH 8, the vaginal fluid from all four donors, as well as the trichomonal hydrolases, each produced color scores of 2.5 or 3. Again, KPQLWP and RKNVY inhibited color production by vaginal fluid hydrolases at this pH, but not as much as at pH 5. The polypeptide, KRQHPG, had weak inhibitory effects on the color production by vaginal fluid hydrolases at either pH tested. In contrast, the largest polypeptide, RPKPQFFGLM, inhibited the color produced by both the vaginal fluid hydrolases and the trichomonal hydrolases, with no wells scoring greater than 1.

Interpretation

The polypeptide RPKPQFFGLM did not exhibit the desired property of selectively inhibiting non-trichomonal vaginal fluid hydrolases, as it decreased the hydrolysis of the substrate (ZRR-MNA) by both trichomonal hydrolases and normal vaginal fluid hydrolases. The other three peptides examined did not decrease color production by trichomonal hydrolases. One of these, KRQHPG, had little inhibitory effect on the vaginal fluid hydrolases but the remaining two polypeptides, KPQLWP and RKNVY, demonstrated selective inhibition of vaginal fluid hydrolases, especially at pH 5.

Experiment 9

This experiment compares certain dipeptides in their ability to selectively inhibit non-trichomonal hydrolases present in whole vaginal fluid and vaginal fluid supernatant with relatively little inhibition of trichomonal hydrolases.

Materials

Swabs containing vaginal fluid specimens collected from four normal, uninfected women Trichomonal hydrolases prepared as described in Preparation A 60-well microwell mini-tray with 20-μL conical microwells Substrate/polypeptide solutions containing 8 mM CBZ-Arg-Arg-MNA acetate (ZRR-MNA), 0.8 mM L-cysteine, 56 mM acetate (pH 5) or TRIS (pH 8) buffer, and 10 mM of one of the following dipeptides:

Lys-proline
Lys-valine
Lys-Lys
No dipeptide (control)

Indicator solution consisting of 0.4 mM para-dimethyl amino cinnamaldehyde, 1% w/v sodium dodecyl sulfate, and 20 mM malic acid (pH 3.4)

Procedure

For each specimen, the vaginal fluid was extracted from the swab by centrifugation, 2 μL of the vaginal fluid supernatant was removed from the microfuge tube, and the remainder of the fluid was mixed to resuspend the particulate matter. For each specimen, 2 μL of the thus reconstituted vaginal fluid was pipetted into each of four microwells, then 2 μL of one of the four substrate/dipeptide combinations was added to each well. The 2 μL of vaginal fluid supernatant from each specimen was mixed with 18 μL of trichomonal hydrolases, and 2 μL of this mixture was mixed with 2 μL of each of the substrate/dipeptide combinations in another set of four wells. After fifteen minutes, 2 μL of indicator solution was added to each well. Ten minutes later, the color in each well was visually scored in 0.5 unit increments using the 0-6 scale presented in Table 2.1.

Results

The results for the tests performed on whole vaginal fluid are shown in Table 9.1 and those for the tests performed with vaginal fluid supernatant are shown in Table 9.2:

TABLE 9.1

Hydrolase Activity in Whole Vaginal Fluid Specimens from Uninfected Women Using Different Dipeptide Inhibitors

|  | Donor A | Donor B | Donor C | Donor D |
| --- | --- | --- | --- | --- |
| No dipeptide | 0.5 | 0 | 0.5 | 2 |
| Lysine-proline | 0 | 0 | 0 | 0 |
| Lysine-valine | 1 | 0 | 0 | 1.5 |
| Lysine-lysine | 1 | 0 | 0 | 2.5 |

TABLE 9.2

Hydrolase Activity in Vaginal Fluid Supernatant Specimens from Uninfected Women Using Different Dipeptide Inhibitors - Trichomonal Hydrolase Added

|  | Donor A | Donor B | Donor C | Donor D |
| --- | --- | --- | --- | --- |
| No dipeptide | 1 | 2 | 1 | 2.5 |
| Lysine-proline | 1 | 1 | 0.5 | 2 |
| Lysine-valine | 1 | 2 | 1 | 2 |
| Lysine-lysine | 1 | 2 | 1 | 2 |

These tables show that three of the four whole vaginal fluid specimens contained measurable hydrolytic activity ("No dipeptide" row in Table 9.1). The dipeptide, lysine-proline, completely inhibited color production by all of those three whole vaginal fluid specimens. The other two dipeptides tested, lysine-valine and lysine-lysine, had little effect on the color produced by the whole vaginal fluid specimens; all of the wells containing either of these dipeptides scored within 0.5 of the corresponding control well for each vaginal fluid donor. Mixtures of normal vaginal fluid supernatants with trichomonal hydrolases produced color scores of one to 2.5 ("No dipeptide" row 1 in Table 9.2). The presence of lysine-proline decreased the color scores produced by trichomonal hydrolases slightly, while lysine-valine or lysine-lysine had little or no inhibitory effect.

Interpretation

Two of the three dipeptides tested, lysine-valine and lysine-lysine, had little effect on the color produced by either vaginal fluid hydrolases or trichomonal hydrolases (color score differences of only 0.5 can be attributed to variations in the amount of particulate matter pipetted to each well). Lysine-proline, however, demonstrated selective inhibition of vaginal fluid hydrolases, with only a small degree of inhibition of trichomonal hydrolases.

Experiment 10

This experiment illustrates the use of a test device containing a strip of filter paper impregnated with the indicator para-dimethylamino-cinnamaldehyde, a substrate conjugate, CBZ-Arg-Arg-MNA (ZRR-MNA), and the enzyme inhibitor E64 in tests on vaginal fluid specimens collected from women attending an STD clinic.

Materials

Swabs (two per donor) containing vaginal fluid specimens collected from women attending an STD clinic, many of whom had bacterial vaginosis, vaginal yeast infections, or other forms of vaginitis, and which were determined to be trichomonas-positive (vaginally infected with *T. vaginalis*) or trichomonas-negative by five-day culture for *T. vaginalis*

100 mM imidazole buffer, pH 7.1

40 mM CBZ-Arg-Arg-MNA (ZRR-MNA) and 0.2 mM trans-epoxysuccinyl-L-leucylamido-(4-guanidino) butane (E64) in ethanol 24 mM para-dimethylamino-cinnamaldehyde (PDMAC) and 5% (w/w) hydroxy-propylcellulose (HPC) in ethanol 3M maleic acid, 2% (w/v) sodium dodecyl sulfate, and 6% (w/v) hydroxypropylcellulose in water Procedure Referring to FIGS. 3a through 3d, test devices were assembled as follows: Two 1-inch-long strips of double-sided tape were affixed in parallel, ¾-inch apart, to a sheet of Mylar 11 that was 5 mils thick. A ³⁄₁₆-inch×⅝-inch strip of Ahlstrom 237 filter paper 12 was affixed to the Mylar sheet with one end (the "upper" end, or the right end as shown in the Figures) of the filter paper strip aligned with the ends of the strips of tape. Approximately 1 μL of the pDMAC mixture was applied as a coating 13 to the upper half of the filter paper strip and allowed to dry. Two μL of the ZRR-MNA mixture 14 was pipetted evenly over ¼-inch of the opposite end of the filter paper strip and allowed to dry. A second sheet of Mylar 20 was affixed to the first sheet, held together by the two strips of double-sided tape, forming a flat sleeve. The filter paper strip 12 was located between the Mylar sheets along the portions that formed the sleeve. A third sheet of Mylar 16, previously coated with a thin dried film 17 of the maleic acid mixture, was affixed to the first sheet of Mylar 11 such that the coated surface was overlying the filter paper strip 12, but temporarily kept from contact with the paper by the second sheet of Mylar 20.

Each swab containing a vaginal fluid specimen from a clinic patient was placed into the sleeve section of a test device. While the test device was held horizontally, a pipet was inserted into the sleeve and 140 μL of buffer was carefully pipetted onto the swab head. The swab was rotated ten times to mix the buffer into the swab head evenly. The swab was inserted deeper into the sleeve until the swab head made firm contact with the end of the filter paper strip, allowing fluid from the swab head to be wicked slowly into the filter paper. After fifteen minutes, the end of the test device was bent and then permitted to snap back, which brought the acid film in contact with the filter paper strip. The reagents in the acid film facilitate a indicator reaction between para-dimethylamino-cinnamaldehyde and any product (MNA) produced by hydrolysis of the substrate by hydrolases present in the specimen. After a five-minute wait, the test device was examined for the development of a pink line on the filter paper strip in the region where the substrate was located.

Results

The results are shown in Table 10.1.

TABLE 10.1

Hydrolase Activity in Vaginal Fluid Specimens Subjects Attending an STD Clinic Using Test Device

| Color | Number of Specimens |
| --- | --- |
| Trichomonas-positive (n = 3): | |
| No pink color | 0 |
| Faint pink color | 0 |
| Distinct pink color | 3 |
| Trichomonas-negative (n = 6): | |
| No pink color | 5 |
| Faint pink color | 1 |
| Distinct pink color | 0 |

Three of the ten vaginal fluid specimens tested were obtained from women with trichomoniasis. The table shows that all three produced a positive test, forming a pink line on the paper strip in the test device. Five of the six specimens from women without trichomoniasis failed to produce any pink color, and one of the six produced only a faint pink color.

Interpretation

This experiment demonstrates that a simple device containing a filter paper strip impregnated with a substrate, indicator and inhibitor is capable of accurately detecting trichomonal hydrolases in vaginal fluid specimens. Other than the buffer solution, all of the reagents were in dry form inside the device. All steps were performed within the device, including dilution of the vaginal fluid specimen with buffer, filtration of the vaginal fluid, hydrolysis of the substrate, and reaction with indicator to produce a visible color. The vaginal fluid, mixed with buffer, was drawn into the filter paper from the swab by wicking. As the fluid traveled laterally through the porous support, the particulate matter was filtered out, and the indicator was mixed in. After this mixture reached the zone containing the substrate and inhibitor, hydrolysis of the substrate occurred if trichomonal hydrolases were present in the vaginal fluid. A fifteen-minute wait provided enough time for the fluid to flow down the strip and for a sufficient amount of substrate to be hydrolyzed by a trichomonas-positive specimen. After acid was applied to the strip, the product of hydrolysis of the substrate reacted with the indicator to produce a clearly visible dark pink line on the strip to indicate a positive result.

Experiment 11

This experiment compares the hydrolysis of CBZ-Arg-Arg-Arg-MNA (ZRRR-MNA) by trichomonal hydrolases at various pH levels over a pH range of 1.9 to 3.4. This experiment also demonstrates a procedure in which a swab is applied to a dried substrate film, then ten minutes later to an indicator film, and the result read directly on the swab.

Materials

Trichomonal hydrolases prepared as described in Preparation D, then diluted to 10% v/v by mixing 50 μL trichomonal hydrolases with 5 μL of 100 mM L-cysteine hydrochloride and 445 μL water 100 mM DL-malic acid solutions adjusted to pH 1.3, 1.6, 1.9, 2.2, 2.5, 2.8, 3.1 or 3.4 using HCl 200 mM CBZ-Arg-Arg-Arg-MNA triacetate (ZRRR-MNA) in ethanol 25% (w/w) hydroxypropylcellulose in ethanol Indicator films prepared as described in Preparation G using 100 mM Fast Red RL dye Procedure The 200 mM ZRRR-MNA solution was mixed with 25% hydroxypropylcellulose solution and additional ethanol to a final concentration of 80 mM ZRRR-MNA and 5% hydroxypropyl-cellulose. Substrate films were made by pipetting 1 µL of a mixture over a circular area approximately ¼-inch in diameter on a sheet of Mylar, and drying under a stream of dry nitrogen. An 80-µL aliquot of a malic acid buffer solution, at each pH listed above, was pipetted into each of eight separate round-bottom wells on a microtiter plate. Eighty µL of 10% trichomonal hydrolase solution was added to each well and mixed thoroughly. Half of the volume in each well (80 µL) was then transferred to a second set of eight wells, into which the swabs were then inserted. After the 80 µL of liquid was absorbed from each well into the respective swab, each swab was rubbed on a substrate film. Ten minutes after the swabs were exposed to substrate, each swab was rubbed on an indicator (Fast Red) film. The intensity of pink color that developed on each swab after one minute was visually scored in 0.5 unit increments using the 0-9 color scale presented in Table 11.1 below. To determine the final pH of the eight mixtures of trichomonal hydrolases and buffer, the pH of the liquid remaining in the first set of eight wells was measured using a pH meter. The experiment was repeated omitting the lowest pH and highest pH wells.

TABLE 11.1

Fast Red RL Color Scores

| Color | Score |
|---|---|
| Colorless or yellow - no pink color | 0 |
| Peach or orange | trace |
| Faint pink | 1 |
| Intermediate intensities of pink | 2-8 |
| Very intense pink/red | 8 |

Results

The results are shown in Table 11.2, and they indicate that the highest hydrolytic activity occurred at approximately pH 2.4:

TABLE 11.2

Trichomonal Hydrolase Activity at Varying pH

| | pH of 100 mM malic acid/final pH in wells | | | | | | | |
|---|---|---|---|---|---|---|---|---|
| Color Scores: | 1.3/1.9 | 1.6/2.1 | 1.9/2.3 | 2.2/2.4 | 2.5/2.6 | 2.8/2.9 | 3.1/3.2 | 3.4/3.4 |
| 1st Experiment | 2 | 4.5 | 5 | 5.5 | 5.5 | 5 | 4.5 | 3 |
| Duplicates | — | 4.5 | 5 | 6 | 5 | 3.5 | 3 | — |

Interpretation

The data in Table 11.2 show that enzymes present in a trichomonal hydrolase solution can hydrolyze ZRRR-MNA at low pH, with a peak of activity of approximately pH 2.4. This feature of trichomonal hydrolases can be exploited in simple diagnostic test that is selective for trichomoniasis, since most hydrolases function very poorly at this low pH.

Experiment 12

This experiment compares the hydrolysis of CBZ-Arg-Arg-Arg-MNA (ZRRR-MNA) by trichomonal hydrolases in four different buffers between pH 2.0 to 2.6.

Materials

Trichomonal hydrolases prepared as described in Preparation D, then diluted to 10% v/v by mixing 100 µL trichomonal hydrolases with 10 µL of 100 mM L-cysteine hydrochloride and 890 µL water 100 mM L-cysteine hydrochloride 100 mM buffer solutions, each at pH 2.0, 2.2, 2.4, and 2.6 a. DL-malic acid b. glycline c. L-threonine d. L-lysine 8 mM CBZ-Arg-Arg-Arg-MNA (ZRRR-MNA) prepared by dilution in water of 200 mM stock in ethanol Indicator films prepared as described in PREPARATION G using 100 mM Fast Red RLdye Procedure Fifty µL of each buffer solution, at pH 2.0, 2.2, 2.4, or 2.6, was pipetted into separate wells of a microtiter plate. Twenty-five µL of 8 mM ZRRR-MNA and 25 µL of 10% trichomonal hydrolase solution were added to each well, and 20 µL were then removed from each well for measurement of final pH. Ten minutes after the mixtures were made, a Dacron swab was inserted into each well to absorb the liquid, then each swab was rubbed on a Fast Red RL film. The intensity of pink color that developed on each swab after five minutes was visually scored in 0.5 unit increments using the 0-9 color scale presented in Table 11.1 of the preceding example.

Results

The results are shown in Table 12.1, which indicates that regardless of the buffer used, the final pH in each well was 0.3 to 0.5 pH units higher than the respective 100 mM buffer stock. Threonine provided the best overall pH control, with the smallest difference between pH of the buffer solution and final pH of the mixture in the wells. At any given final pH, the color scores were the highest with threonine as the buffer: at pH 2.4, the well with threonine scored 6.0 as compared to 5.0 for glycine and 4.5 for malic acid; at pH 2.7, the threonine well scored 6.5 as compared to 6.0 for glycine and 5.5 for malic acid; at pH 2.9, the wells with threonine, glycine or malic acid all scored 6.0.

TABLE 12.1

Trichomonal Hydrolase Activity at Varying pH

| | pH 2.0 Buffer | | pH 2.2 Buffer | | pH 2.4 Buffer | | pH 2.6 Buffer | |
|---|---|---|---|---|---|---|---|---|
| | Final pH | Score | Final pH | Score | Final pH | Score | Final pH | Score |
| DL-malic acid | pH 2.4 | 4.5 | pH 2.7 | 5.5 | pH 2.8 | 6.0 | pH 2.9 | 6.0 |
| Glycine | pH 2.4 | 5.0 | pH 2.6 | 6.0 | pH 2.7 | 6.0 | pH 2.9 | 6.0 |
| L-threonine | pH 2.3 | 3.5 | pH 2.4 | 6.0 | pH 2.7 | 6.5 | pH 2.9 | 6.0 |
| L-lysine | pH 2.3 | 3.0 | pH 2.5 | 4.5 | pH 2.9 | 5.0 | pH 3.0 | 5.5 |

Interpretation

Experiment 11 demonstrated maximal enzyme activity by trichomonal hydrolases at pH 2.4. The ideal buffer would support maximal enzyme activity by trichomonal hydrolases while providing adequate buffering capacity at this pH. Insufficient buffering, with the resultant higher pH, could lead to both decreased activity by trichomonal hydrolases and increased activity by non-trichomonal hydrolases. Furthermore, high concentrations of buffer may inhibit trichomonal hydrolase activity.

The present experiment shows that all four of the buffers tested at pH 2.4 were compatible with trichomonal hydrolase activity, although enzyme activity was not as high with lysine as with the other three buffers. The best buffering capacity under the conditions of this test was demonstrated by threonine and malic acid. Between these two buffers, threonine provided the best pH control and supported the highest hydrolase activity.

Experiment 13

This experiment tests compares a series of peptide substrate conjugates in terms of the ability of trichomonal hydrolases to hydrolyze these substrates at low pH.

Materials

Trichomonal hydrolases prepared as described in Preparation D 200 mM L-threonine buffer, pH 2.4

2 mM L-cysteine hydrochloride in water

Pooled normal vaginal fluid supernatant (NVS) prepared as follows: vaginal fluid specimens collected on dacron swabs from normal, uninfected women were centrifuged to extract the undiluted fluid from the swabs and to pellet the particulate matter, and then the supernatants were pooled and frozen until use 0.2 mg/mL Fast Garnet GBC sulfate, dissolved in water no more than an hour before being used 2% sodium dodecyl sulfate in 500 mM pH 5 acetate buffer (SDS/acetate)

2 mM solutions of each of a series of substrates listed below in threonine buffer; hydrophobic peptide substrates were initially dissolved in a small amount of DMSO, then diluted to 2 mM in threonine buffer Procedure 1. Assays without Vaginal Fluid Present Forty µL of each substrate was pipetted into duplicate wells of a microtiter plate. The plate was covered with tape, placed into a 25° C. incubator, and allowed to warm. A diluted enzyme mixture was prepared by mixing one part (v/v) freshly-thawed trichomonal hydrolase solution to nine parts 2 mM L-cysteine solution. Forty µL of this mixture was added to one well of each pair of duplicate wells. For negative controls, 40 µL of 2 mM L-cysteine was added to the second well in each pair of duplicate wells. The plate was returned to the incubator and incubated for ten minutes. Forty µL of SDS/acetate solution was added to each well, followed by 40 µL of Fast Garnet solution. The intensity of color that developed in each well after five minutes was visually scored using the color scale presented in Table 13.1.

TABLE 13.1

Color Scores

| Color Score | Interpretation |
|---|---|
| − | No red color produced |
| + | Clearly visible red color produced |
| ++ | Moderately intense red color produced |
| +++ | Very intense red color produced |

Results

1. Assays without Vaginal Fluid Present

Test results for 61 peptide substrates are listed in Table 13.2. Of these substrates, only thirteen were hydrolyzed by trichomonal hydrolases. Of the thirteen substrates hydrolyzed, only nine produced suitably intense color (scoring either ++ or +++).

TABLE 13.2

Trichomonal Hydrolase Activity on Various Peptide Substrates

| Peptide Substrate | Color Score |
|---|---|
| D-Val-Leu-Arg-MNA | +++ |
| CBZ-Arg-Arg-Arg-MNA | +++ |
| CBZ-Leu-Arg-MNA | +++ |
| CBZ-Val-Arg-MNA | +++ |
| CBZ-Phe-Arg-MNA | ++ |
| BZ-Phe-Val-Arg-MNA | ++ |
| CBZ-Arg-Arg-MNA | ++ |
| D-Val-Leu-Lys-MNA | ++ |
| CBZ-Ala-Arg-Arg-MNA | ++ |
| CBZ-Val-Leu-Arg-MNA | + |
| CBZ-Leu-Arg-Arg-MNA | + |
| CBZ-Val-Lys-Lys-Arg-MNA | + |
| CBZ-Lys-Lys-Arg-MNA | + |
| CBZ-Lys-βNA | − |
| BZ-DL-Arg-βNA | − |
| BZ-Arg-MNA | − |
| CBZ-Arg-MNA | − |
| Arg-Arg-βNA | − |
| CBZ-Arg-Arg-βNA | − |
| BZ-Pro-Phe-Arg-βNA | − |
| BOC-Gln-Ala-Arg-MNA | − |
| CBZ-Gly-Gly-Arg-MNA | − |
| CBZ-Gly-Pro-Arg-MNA | − |
| Phe-Arg-βNA | − |
| Pro-Arg-MNA | − |

TABLE 13.2-continued

Trichomonal Hydrolase Activity on Various Peptide Substrates

| Peptide Substrate | Color Score |
| --- | --- |
| Gly-Arg-βNA | − |
| Gly-Arg-MNA | − |
| BOC-Gln-Ala-Ala-MNA | − |
| CBZ-Arg-Gly-Phe-Leu-MNA | − |
| CBZ-Gly-Gly-Leu-βNA | − |
| CBZ-Gly-Gly-Phe-βNA | − |
| Gln-Gly-Phe-MNA | − |
| Ala-Ala-βNA | − |
| Gly-Phe-MNA | − |
| Gly-Phe-βNA | − |
| Gly-Gly-βNA | − |
| Gly-Pro-MNA | − |
| Gly-Trp-βNA | − |
| His-Ser-MNA | − |
| Leu-Ala-βNA | − |
| Lys-Ala-βNA | − |
| Ser-Met-βNA | − |
| Ser-Tyr-βNA | − |
| Arg-βNA | − |
| Arg-MNA | − |
| Lys-βNA | − |
| Ala-βNA | − |
| Gly-βNA | − |
| His-βNA | − |
| Ile-βNA | − |
| Leu-βNA | − |
| Leu-MNA | − |
| Leu-MNA | − |
| Phe-βNA | − |
| Phe-MNA | − |
| Pro-βNA | − |
| Pro-MNA | − |
| Hyp-βNA | − |
| Trp-βNA | − |
| Ser-βNA | − |
| Val-βNA | − |

2. Assays without Vaginal Fluid Present

Of the nine substrates hydrolyzed by trichomonal hydrolases to produce an intense pink color (scoring ++ or +++) in the absence of vaginal fluid supernatant, only four produced intense pink color when vaginal fluid supernatant was present. These results are listed in Table 13.3.

TABLE 13.3

Trichomonal Hydrolase Activity on Peptide Substrates in Vaginal Fluid Supernatant

| Peptide Substrate | Color Score |
| --- | --- |
| D-Val-Leu-Arg-MNA | +++ |
| CBZ-Arg-Arg-Arg-MNA | ++ |
| CBZ-Leu-Arg-MNA | +++ |
| CBZ-Val-Arg-MNA | ++ |
| CBZ-Phe-Arg-MNA | + |
| BZ-Phe-Val-Arg-MNA | + |
| CBZ-Arg-Arg-MNA | + |
| D-Val-Leu-Lys-MNA | + |
| CBZ-Ala-Arg-Arg-MNA | + |

Interpretation

Only thirteen of the 61 peptide substrates tested generated color in the presence of trichomonal hydrolases at very low pH. Of these, only nine produced sufficient color. Four of these nine substrates were readily hydrolyzed by trichomonal hydrolases in the presence of vaginal fluid: D-Val-Leu-Arg-MNA (VLR-MNA); CBZ-Leu-Arg-MNA (ZLR-MNA); CBZ-Arg-Arg-Arg-MNA (ZRRR-MNA); and CBZ-Val-Arg-MNA (ZVR-MNA).

Experiment 14

This experiment compares vaginal fluid specimens from normal, uninfected women with vaginal fluid specimens to which trichomonal hydrolases have been added, in terms of the action of these specimens on four peptide substrates at low pH. This example also illustrates a test procedure involving applying a swab with specimen to a substrate and indicator and subsequently reading the result directly on the swab.

Materials

Trichomonal hydrolases prepared as described in Preparation D

Cotton swabs (two per donor) containing vaginal fluid specimens collected from normal, uninfected women.

200 mM L-threonine buffer, pH 2.4

Peptide substrates:

400 mM D-Val-Leu-Arg-MNA (VLR-MNA) in ethanol with 10% (v/v) 6M HCl 400 mM CBZ-Leu-Arg-MNA (ZLR) in methanol with 10% (v/v) dimethylformamide 400 mM CBZ-Arg-Arg-Arg-MNA (ZRRR-MNA) in ethanol 400 mM CBZ-Val-Arg-MNA (ZVR) in methanol with 10% (v/v) dimethylformamide 2 mM L-cysteine hydrochloride in water 25% (w/w) hydroxypropylcellulose in ethanol Indicator films prepared as described in PREPARATION G using either 10 mM Fast Garnet or 70 mM Fast Red RL diazonium dye Procedure 1. Preparation of Substrate Films Mixtures were made of the 400 mM substrate stock solutions, 25% hydroxy-propylcellulose solution, 200 mM L-cysteine, along with additional ethanol to a final concentration of 150-320 mM substrate, 20 mM Lcysteine, and 2-5% hydroxypropyl-cellulose. Substrate films were made by pipetting 1 µL of a mixture over a circular area approximately ¼-inch in diameter on a sheet of Mylar, and drying under a stream of dry nitrogen. The dried films were stored in a container with desiccant until used.

2. Comparison of Substrates Using Vaginal Fluid Specimens on Cotton Swabs

For each pair of vaginal fluid specimens from a donor, one swab was rubbed on one substrate film and the other swab was rubbed on a different substrate film; two substrates were compared at a time. The concentrations of the substrates varied from 150 mM to 320 mM in the solutions used to make the substrate films, but each specific comparison matched equimolar concentrations of substrates (as specified in Tables 14.1, 14.2, and 14.3 below). In the swabs, the substrate was diluted by vaginal fluid and buffer, and the final concentration of substrate in the swab tip was estimated to be ⅟₆₀ of the concentration of substrate in the solutions used to make the films. Immediately after each swab was rubbed on a substrate film, a 35-µL drop of threonine buffer was applied to the plastic where the substrate film had been, and the swab was rubbed on the same spot again until the buffer was absorbed into the swab. The swabs were left lying on the plastic for ten minutes, then each swab was rubbed on a Fast Red or Fast Garnet film. For the comparisons between ZLR and ZVR, and between VLR-MNA and ZRRR-MNA, films made with 10 mM Fast Garnet were used; for the comparison between ZVR and VLR-MNA, films made with 70 mM Fast Red were used. The intensity of pink color that developed on each swab after two minutes was visually scored using the 0-9 color scale presented in Table 11.1 above; fractional scores such as 1.3 were used when color intensities between swabs differed only slightly.

3. Comparison of Substrates Using Trichomonal Hydrolases Added to Vaginal Fluid Specimens on Cotton Swabs In this part of the experiment, 20 μL of trichomonal hydrolases was applied to the tip of each swab containing vaginal fluid just prior to running the assay. Otherwise, the procedure was exactly the same as for the swabs containing only vaginal fluid.

Results

The results are shown in the following tables: Table 14.1 compares ZLR with ZVR at 320 mM, Table 14.2 compares VLR-MNA with ZVR at 150 mM, and Table 14.3 compares VLR-MNA with ZRRR-MNA at 200 mM.

TABLE 14.1

Peptide Substrate Comparisons

| Vaginal Fluid Specimens | ZLR 320 mM | ZVR 320 mM |
|---|---|---|
| Normal (n = 4) | 0 to Trace | Trace to 1.5 |
| Hydrolases added (n = 4) | Trace to 1 | 1 to 5 |

TABLE 14.2

Peptide Substrate Comparisons

| Vaginal Fluid Specimens | VLR-MNA 150 mM | ZVR 150 mM |
|---|---|---|
| Normal (n = 3) | 0 | 2.5 to 3 |
| Hydrolases added (n = 2) | 2 to 2.5 | 4.5 to 5 |

TABLE 14.3

Peptide Substrate Comparisons

| Vaginal Fluid Specimens | VLR-MNA 200 mM | ZRRR-MNA 200 mM |
|---|---|---|
| Normal (n = 6) | 0 to Trace | 0 to Trace |
| Hydrolases added (n = 5) | 1 to 4 | 1 to 4 |

Table 14.1 shows that when ZLR was compared with ZVR at 320 mM, the color produced by ZLR was too faint in swabs containing vaginal fluid plus trichomonal hydrolases, scoring only one or less. ZVR scored 1 or higher in all of the specimens with hydrolases added, but also scored as high as 1.5 in normal vaginal fluid specimens without hydrolases added.

In Table 14.2, the concentration was reduced from 320 mM to 150 mM in an attempt to decrease the sensitivity of ZVR to endogenous hydrolases present in normal vaginal fluid. The results in this table show that ZVR again produced pink color in normal specimens, this time scoring over 2, while VLR-MNA produced scores of zero in normal specimens, and scores of 2 or higher in specimens to which trichomonal hydrolases had been added.

In Table 14.3, VLR-MNA is compared with ZRRR-MNA at an increased concentration of 200 mM to improve the color intensity from trichomonal hydrolases. Both substrates produced zero to trace color in swabs containing only vaginal fluid, and color scores of 1 or more in swabs containing vaginal fluid with trichomonal hydrolases added.

Interpretation

For clinical utility, it is essential that the substrates produce no more than trace color (less than a score of 1) in specimens containing vaginal fluid from normal, uninfected women, and color intensities scoring at least 1 in swabs to which trichomonal hydrolases have been added to the vaginal fluid. ZLR proved to be a poor substrate compared to ZVR, sometimes producing color intensity scores of less than 1 in swabs which had trichomonal hydrolases added to the vaginal fluid. ZVR, in turn, was less desirable than VLR-MNA, due to unacceptably high reactivity with hydrolases in present in normal vaginal fluid specimens, scoring as high as three in these swabs. Both VLR-MNA and ZRRR-MNA produced favorable results in this experiment.

Experiment 15

This experiment compared two testing procedures using vaginal fluid specimens with trichomonal hydrolases added to the swabs: a) application of the diazonium dye to the swab immediately after the swab was rubbed on the substrate film ("one-phase" application of reagents to the swab), and b) application of the diazonium dye to the swab ten minutes after the swab was rubbed on the substrate film ("two-phase" application of reagents to the swab). The goal was to determine if the nearly simultaneous "one-step" application of the substrate and diazonium dye would affect the intensity of pink color produced.

Materials

Trichomonal hydrolases prepared as described in Preparation D

Cotton swabs (two per donor) containing vaginal fluid specimens collected from normal, uninfected women 200 mM L-threonine buffer, pH 2.4

Substrate films prepared as described in Preparation E using 80 mM ZRRR-MNA

Indicator films prepared as described in Preparation G using 10 mM Fast Garnet diazonium dye Procedure Immediately before each assay, 10 μL of trichomonal hydrolases was applied to each vaginal fluid specimen. One swab from each pair of specimens was rubbed on a substrate film, on a Fast Garnet film, and on a 35 μL drop of threonine buffer until the buffer was absorbed into the swab ("one-phase" application of reagents). At the same time, the second swab from each pair of specimens was treated likewise, but omitting the Fast Garnet film. After ten minutes, the second swab from each pair was rubbed on a Fast Garnet film ("two-phase" application of reagents). After another thirty seconds, the intensity of pink color that developed on both swabs was visually scored in 0.5 unit increments using the 0-9 color scale presented in Table 11.1.

Results

The results are shown in Table 15.1.

TABLE 15.1

Comparison of Application Methods

| Vaginal Fluid Specimens | One-Phase | Two-Phase |
|---|---|---|
| Donor A | 1 | 3 |
| Donor B | 1 | 2 |
| Donor C | 1 | 3 |

TABLE 15.1-continued

Comparison of Application Methods

| Vaginal Fluid Specimens | One-Phase | Two-Phase |
|---|---|---|
| Donor D | 1 | 2 |
| Donor E | 1 | 2 |

The data in Table 15.1 show that all five swabs in which the diazonium dye and substrate were applied nearly simultaneously ("one-phase" application of reagents) produced a color score of 1 after ten minutes, whereas the five swabs in which the diazonium dye was applied ten minutes after the substrate ("two-phase" application of reagents) scored 2 or 3.

Interpretation

In both procedures, the intensity of the pink color produced was scored ten and a half minutes after the substrate was applied to each swab, but the pink color was less intense when the diazonium dye was applied at the start rather than at the end of the ten-minute period. Either procedure will detect trichomonal hydrolases, but the "two-phase" procedure produces a more intense color.

Experiment 16

This experiment compared the responses of two peptide-based substrates at low pH to specimens from women attending an STD clinic, including both trichomonas-positive and trichomonas-negative specimens.

Materials

Dacron swabs (two per donor) containing vaginal fluid specimens collected from women subjects, many of whom had bacterial vaginosis, vaginal yeast infections, or other forms of vaginitis, and which were determined to be trichomonas-positive (vaginally infected with *T. vaginalis*) or trichomonas-negative by 5-day culture for *T. vaginalis*

200 mM L-threonine buffer, pH 2.4

Substrate films prepared as described in Preparation E using 200 mM ZRRR-MNA, and as described in Preparation F using 200 mM VLR-MNA Indicator films prepared as described in Preparation G using 10 mM Fast Garnet diazonium dye Procedure For each pair of vaginal fluid specimens from a clinic patient, one swab was rubbed on ZRRR-MNA film and the other swab was rubbed on VLR-MNA film. Immediately after each swab was rubbed on a substrate film, the swab was rubbed on a 35 µL drop of threonine buffer until the buffer was absorbed into the swab. The swabs were left lying on the plastic for ten minutes, then each swab was rubbed on a Fast Garnet film. The intensity of pink color that developed on each swab after thirty seconds was visually scored in 0.5-unit increments using the 0-9 color scale presented in Table 11.1.

Results

The results are shown in Table 16.1.

TABLE 16.1

Comparison of Substrate Responses

| Vaginal Fluid Specimens | ZRRR-MNA | VLR-MNA |
|---|---|---|
| *Trichomonas*-positive (n = 8): | | |
| Scoring 0 | 0 | 0 |
| Scoring Trace | 0 | 0 |
| Scoring 1-2 | 4 | 4 |
| Scoring 3-4 | 3 | 2 |
| Scoring >4 | 1 | 2 |
| *Trichomonas*-negative (n = 28): | | |
| Scoring 0 | 15 | 23 |
| Scoring Trace | 5 | 0 |
| Scoring 1-2 | 6 | 4 |
| Scoring 3-4 | 2 | 1 |
| Scoring >4 | 0 | 0 |

The data in Table 16.1 show that both ZRRR-MNA and VLR-MNA were hydrolyzed by the hydrolases present in vaginal fluid specimens from women with trichomoniasis. The intensity of pink color produced by either peptide substrate was nearly equivalent in these paired specimens. For either substrate, 8 of 8 (100%) trichomonas-positive swabs produced pink color, half scoring 1-2 and half scoring 3 or higher. In specimens from women that did not have trichomoniasis, 13 of 28 (46%) swabs treated with ZRRR-MNA produced pink color, whereas only 5 of 28 (18%) swabs treated with VLR-MNA produced pink color.

Interpretation

Both peptide substrates were hydrolyzed efficiently by hydrolases present in vaginal fluid specimens from women with trichomoniasis, but VLR-MNA was hydrolyzed less often than ZRRR-MNA by trichomonas-negative specimens.

Experiment 17

This experiment examines the effect of increasing the amount of D-Val-Leu-Arg-MNA (VLR-MNA) on the intensity of pink color produced on cotton swabs containing trichomonal hydrolases.

Materials

Trichomonal hydrolases prepared as described in Preparation D

Pooled normal vaginal fluid supernatant prepared as follows: vaginal fluid specimens collected on Dacron swabs from normal, uninfected women were centrifuged to extract the undiluted fluid from the swabs and to pellet the particulate matter, and then the supernatants were pooled and frozen until use 100 mM L-cysteine hydrochloride in water 200 mM L-threonine buffer, pH 2.4

Substrate film dots prepared as described in Preparation F using 100 mM VLR-MNA

Indicator films prepared as described in Preparation G using 10 mM Fast Garnet diazonium dye Procedure Solution A, containing 10% v/v trichomonal hydrolases and 2 mM L-cysteine, was prepared by mixing 20 µL of trichomonal hydrolases with 4 µl of 100 mM L-cysteine and 176 µL of water, and Solution B, containing 20% v/v trichomonal hydrolases, 5% v/v normal vaginal fluid supernatant and 2 mM L-cysteine, was prepared by mixing 40 μL of trichomonal hydrolases with 10 μL of normal vaginal fluid supernatant, 4 μL of 100 mM L-cysteine and 176 μL of water. Several 35 μL drops, each of Solution A, Solution B, and threonine buffer were individually pipetted onto discrete, separated areas on a sheet of Mylar. Individual cotton swabs were rubbed on a drop of either Solution A or Solution B, then on one, two or three dots of substrate, and then on a drop of buffer. After ten minutes, each swab was rubbed on an indicator film. The intensity of pink color that developed on each swab after thirty seconds was visually scored in 0.5 unit increments using the 0-9 color scale presented in Table 11.1.

Results

The results are shown in Table 17.1.

TABLE 17.1

Comparison of Substrate Amounts

| Test Solution | One dot of Substrate | Two dots of Substrate | Three dots of Substrate |
|---|---|---|---|
| Solution A | 5.5 | 7 | 9 |
| Solution B | 2.5 | 4 | 5.5 |

The data in Table 17.1 show that the intensity of pink color produced by trichomonal hydrolases increased with increasing amounts of substrate, whether or not vaginal fluid was present. Solution A, which contained trichomonal hydrolases but no vaginal fluid, produced a moderately dark pink color scoring 5.5 when a single dot of VLR-MNA film was applied to the swab, and a very intense dark pink color scoring 9 when a triple amount of VLR-MNA was applied to the swab. Likewise, the intensity of pink color produced by Solution B, which contained trichomonal hydrolases and vaginal fluid, scored 2.5 with a single dot of VLR-MNA, 4 with two dots of VLR-MNA, and 5.5 with three dots of VLR-MNA.

Interpretation

The intensity of pink color produced by trichomonal hydrolases increased with increasing amounts of substrate, whether or not vaginal fluid was present. Therefore, to maximize the sensitivity of detection of trichomonal hydrolases in vaginal fluid specimens on swabs, a high concentration of substrate should be used. Dry films are a very effective means to deliver the substrate to a swab.

Experiment 18

This experiment compares two diazonium dyes in terms of color development ten minutes after substrate had been applied to swabs, using swabs containing normal vaginal fluid specimens and swabs containing normal vaginal fluid to which trichomonal hydrolases added. The goal was to determine which diazonium dye maximizes the pink color produced on trichomonas-positive swabs and minimizes the pink color produced on trichomonas-negative swabs.

Materials

Trichomonal hydrolases prepared as described in Preparation D

Cotton swabs (two per donor) containing vaginal fluid specimens collected from normal, uninfected women 200 mM L-threonine buffer, pH 2.4

Substrate films prepared as described in Preparation F using 200 mM VLR-MNA

Indicator films prepared as described in Preparation G using 10 mM Fast Garnet diazonium dye Procedure 1. Comparison of diazonium dyes using vaginal fluid specimens from normal, uninfected women Each vaginal fluid specimen was rubbed on a dried substrate film and then rubbed on a 35-μL drop of threonine buffer until the buffer was absorbed into the swab. After a ten-minute wait, one swab from each pair was rubbed on a Fast Red RL film and the other swab was rubbed on a Fast Garnet film. The intensity of pink color that developed on each swab after thirty seconds was visually scored using the 0-9 color scale presented in Table 11.1; fractional scores such as 0.3 were used when pink color intensities between swabs differed only slightly.

2. Comparison of diazonium dyes using trichomonas-positive swabs created by adding trichomonas hydrolases to vaginal fluid specimens In this part of the experiment, 20 μL of trichomonal hydrolases was applied to the tip of each swab containing a vaginal fluid specimen just prior to running the assay. Otherwise, the procedure was exactly the same as for the swabs containing only vaginal fluid.

Results

The results are shown in Table 18.1.

TABLE 18.1

Comparison of Diazonium Dyes

| Vaginal Fluid Specimens | Fast Red RL | Fast Garnet |
|---|---|---|
| Specimens from Normal, Uninfected Women (n = 5): | | |
| Scoring 0 | 4 | 5 |
| Scoring Trace | 1 | 0 |
| Scoring 1-2 | 0 | 0 |
| Scoring 3-4 | 0 | 0 |
| Scoring >4 | 0 | 0 |
| Trichomonal hydrolases added (n = 5): | | |
| Scoring 0 | 0 | 0 |
| Scoring Trace | 1 | 3 |
| Scoring 1-2 | 2 | 1 |
| Scoring 3-4 | 1 | 1 |
| Scoring >4 | 1 | 0 |

The data in Table 18.1 show that swabs containing vaginal fluid from normal, uninfected women produced very little pink color when treated with substrate and buffer, followed ten minutes later by either Fast Red RL or Fast Garnet. Four of five swabs treated with Fast Red RL, and five of five swabs treated with Fast Garnet, had no visible pink color when the swabs were examined thirty seconds after the diazonium dye was applied; one of the five swabs treated with Fast Red RL produced a trace amount of pink color. When a small amount of trichomonal hydrolases was added to vaginal fluid specimens to simulate trichomonas-positive specimens, all of the swabs produced at least a trace amount of pink color. The simulated trichomonas-positive swabs treated with Fast Red RL produced more intense pink color than those treated with Fast Garnet. Of five simulated trichomonas-positive swabs treated with Fast Red RL, two scored three or higher, two scored 1-2, and only one had trace pink color. Of five simulated trichomonas-positive swabs treated with Fast Garnet, one scored three or higher, one scored 1-2, and three had only trace pink color.

Interpretation

Either Fast Red RL or Fast Garnet can be used in a device to detect trichomonal hydrolases. Both dyes produced little or no pink color in swabs that contained vaginal fluid from normal, uninfected women, and both produced pink color in swabs that had trichomonal hydrolases added to the vaginal fluid. However, Fast Red RL produced more intense pink color than Fast Garnet in the trichomonal hydrolase-containing swabs.

Experiment 19

This is a further study of the two diazonium dyes studied in Experiment 18, using however actual vaginal fluid specimens from women attending an STD clinic.

Materials

Dacron or cotton swabs (two per donor) containing vaginal fluid specimens collected from women attending an STD clinic, many of whom had bacterial vaginosis, vaginal yeast infections, or other forms of vaginitis, and which were determined to be trichomonas-positive (vaginally infected with *T. vaginalis*) or trichomonas-negative by five-day culture for *T. vaginalis*

200 mM L-threonine buffer, pH 2.4

Substrate films prepared as described in Preparation F using 200 mM VLR-MNA

Indicator films prepared as described in Preparation G using either 10 mM Fast Garnet or 70 mM Fast Red RL diazonium dye Procedure Each of the two vaginal fluid specimens from each clinic patient was rubbed on a substrate film and then rubbed on a 35 µL drop of threonine buffer until the buffer was absorbed into the swab. After a ten-minute wait, one swab from each pair was rubbed on a Fast Red RL film and the other swab was rubbed on a Fast Garnet film. The intensity of pink color that developed on each swab after thirty seconds was visually scored in 0.5 unit increments using the 0-9 color scale presented in Table 11.1.

Results

The results are shown in Table 19.1.

TABLE 19.1

Comparison of Diazonium Dyes

| Vaginal Fluid Specimens | Fast Red RL | Fast Garnet |
|---|---|---|
| *Trichomonas*-positive (n = 12): | | |
| Scoring 0 | 0 | 0 |
| Scoring Trace | 0 | 0 |
| Scoring 1-2 | 2 | 5 |
| Scoring 3-4 | 6 | 6 |
| Scoring >4 | 4 | 1 |
| *Trichomonas*-negative (n = 39): | | |
| Scoring 0 | 25 | 28 |
| Scoring Trace | 8 | 8 |
| Scoring 1-2 | 6 | 3 |
| Scoring 3-4 | 0 | 0 |
| Scoring >4 | 0 | 0 |

The data in Table 19.1 show that swabs containing vaginal fluid collected from twelve women with trichomoniasis produced more intense pink color when Fast Red RL rather than Fast Garnet was used to develop the color. All of the trichomonas-positive specimens produced pink color scores of 1 or higher regardless of which diazonium dye was used, but four of the swabs treated with Fast Red RL scored over 4, whereas only one of the swabs treated with Fast Garnet scored over 4. Most of the swabs containing vaginal fluid specimens from 39 women without trichomoniasis produced no more than trace color with either diazonium dye.

Interpretation

Consistently with the results Experiment 18, Fast Red RL produced more intense pink color than Fast Garnet in trichomonas-positive swabs (containing vaginal fluid from women with trichomoniasis).

Experiment 20

This experiment compared two procedures using swabs containing vaginal fluid specimens collected from women attending an STD clinic: (a) application of the buffer after the swab is rubbed on the substrate film; and (b) application of the buffer to the substrate film prior to rubbing the swab on the film. The goal was to determine which procedure maximizes the pink color produced on trichomonas-positive swabs and minimizes the pink color produced on trichomonas-negative swabs.

Materials

Cotton swabs (two per donor) containing vaginal fluid specimens collected from women attending an STD clinic, many of whom had bacterial vaginosis, vaginal yeast infections, or other forms of vaginitis, and which were determined to be trichomonas-positive (vaginally infected with *T. vaginalis*) or trichomonas-negative by five-day culture for *T. vaginalis*

200 mM L-threonine buffer, pH 2.4

Substrate films prepared as described in Preparation F using 200 mM VLR-MNA

Indicator films prepared as described in Preparation G using either 10 mM Fast Garnet or 70 mM Fast Red diazonium dye Procedure One of the two vaginal fluid specimens from each clinic patient was rubbed on a substrate film and then rubbed on a 35 µL drop of threonine buffer until the buffer was absorbed into the swab (buffer-after-substrate procedure). The second swab from each pair was rubbed on the substrate film immediately after a 35 µL drop of threonine buffer was applied to the substrate film, so both the buffer and the substrate were simultaneously mixed into the swab (buffer-with-substrate procedure). After a ten-minute wait, each swab was rubbed on a Fast Red RL film. The intensity of pink color that developed on each swab after thirty seconds was visually scored in 0.5 unit increments using the 0-9 color scale presented in Table 11.1.

Results

The results are shown in Table 20.1.

TABLE 20.1

Comparison of Application Procedures

| Vaginal Fluid Specimens | Buffer After substrate | Buffer With Substrate |
|---|---|---|
| *Trichomonas*-positive (n = 12): | | |
| Scoring 0 | 3 | 4 |
| Scoring Trace | 1 | 1 |
| Scoring 1-2 | 3 | 1 |

TABLE 20.1-continued

Comparison of Application Procedures

| Vaginal Fluid Specimens | Buffer After substrate | Buffer With Substrate |
|---|---|---|
| Scoring 3-4 | 1 | 2 |
| Scoring >4 | 4 | 4 |
| Trichomonas-negative (n = 31): | | |
| Scoring 0 | 25 | 31 |
| Scoring Trace | 4 | 0 |
| Scoring 1-2 | 2 | 0 |
| Scoring 3-4 | 0 | 0 |
| Scoring >4 | 0 | 0 |

The data in Table 20.1 show that nine of the twelve trichomonas-positive specimens processed using the buffer-after-substrate procedure produced some pink color, with five scoring 3 or higher. Eight of the twelve trichomonas-positive specimens processed using the buffer-with-substrate procedure produced some pink color, with six scoring 3 or higher. The effect of procedure was greater for the trichomonas-negative specimens. Of the trichomonas-negative specimens, all 31 scored zero (the desired negative test result) with the buffer-with-substrate procedure, but only 25 scored zero with the buffer-after-substrate procedure.

Interpretation

Compared to the buffer-after-substrate procedure, the buffer-with-substrate procedure diminished the number of false-positive test results from trichomonas-negative specimens while maintaining the desired production of pink color by trichomonas-positive specimens.

Experiment 21

Using swabs containing vaginal fluid specimens collected from women attending an STD clinic, this experiment examined the effect of decreasing the test duration from ten minutes to five minutes.

Materials

Cotton swabs (two per donor) containing vaginal fluid specimens collected from women attending an STD clinic, many of whom had bacterial vaginosis, vaginal yeast infections, or other forms of vaginitis, and which were determined to be trichomonas-positive (vaginally infected with *T. vaginalis*) or trichomonas-negative by five-day culture for *T. vaginalis*

200 mM L-threonine buffer, pH 2.4

Substrate films prepared as described in Preparation F using 200 mM VLR-MNA

Indicator films prepared as described in Preparation G using 10 mM Fast Garnet diazonium dye Procedure Each of the two vaginal fluid specimens from each clinic patient was rubbed on a substrate film just after a 35 µL drop of threonine buffer had been applied to the substrate film. After a five-minute wait, one swab was rubbed on a Fast Red RL film. After another five minutes, the second swab was rubbed on a Fast Red RL film. The intensity of pink color that developed on each swab after thirty seconds was visually scored in 0.5 unit increments using the 0-9 color scale presented in Table 11.1.

Results

The results are shown in Table 21.1.

TABLE 21.1

Comparison of Application Procedures

| Vaginal Fluid Specimens | 5 Minutes | 10 Minutes |
|---|---|---|
| Trichomonas-positive (n = 17): | | |
| Scoring 0 | 2 | 2 |
| Scoring Trace | 1 | 1 |
| Scoring 1-2 | 7 | 2 |
| Scoring 3-4 | 1 | 5 |
| Scoring >4 | 6 | 7 |
| Trichomonas-negative (n = 53): | | |
| Scoring 0 | 49 | 43 |
| Scoring Trace | 4 | 8 |
| Scoring 1-2 | 0 | 1 |
| Scoring 3-4 | 0 | 0 |
| Scoring >4 | 0 | 0 |

The data in Table 21.1 show that the five-minute and ten-minute tests each produced fifteen positive test results (swabs scoring of one or higher) from seventeen paired specimens containing vaginal fluid collected from women with trichomoniasis. However, the intensity of pink color was less intense on the swabs given the five-minute test. Twelve of seventeen trichomonas-positive swabs given ten-minute tests scored 3 or higher, whereas only seven of seventeen trichomonas-positive swabs given five-minute tests scored 3 or higher. The five-minute test produced fewer false-positive test results than the ten-minute test, however. Of 53 paired trichomonas-negative specimens tested, the five-minute test produced 49 negative results (yellow swab tip) and four trace results, whereas the ten-minute test produced 43 negative results, eight trace results, and one weak positive result.

Interpretation

This experiment demonstrated that an accurate five-minute swab-based "rub-and-read" test for vaginal trichomoniasis can be made using a pH 2.4 buffer and two dry rub-off films.

Experiment 22

This experiment compared cotton swabs with Dacron swabs in terms of the intensity of pink color, using swabs containing vaginal fluid specimens collected from women attending an STD clinic.

Materials

Swabs (on cotton and one Dacron from each donor) containing vaginal fluid specimens collected from women attending an STD clinic, many of whom had bacterial vaginosis, vaginal yeast infections, or other forms of vaginitis, and which were determined to be trichomonas-positive (vaginally infected with *T. vaginalis*) or trichomonas-negative by five-day culture for *T. vaginalis*

200 mM L-threonine buffer, pH 2.4

Substrate films prepared as described in Preparation F using 200 mM VLR-MNA

Indicator films prepared as described in Preparation G using 10 mM Fast Garnet diazonium dye Procedure Each of the two vaginal fluid specimens from each clinic patient, one collected on a cotton swab and the other on a Dacron swab, was rubbed on a substrate film just after a 35-μL drop of threonine buffer had been applied to the substrate film. After a five-minute wait, one swab was rubbed on a Fast Red RL film. The intensity of pink color that developed on each swab after thirty seconds was visually scored in 0.5 unit increments using the 0-9 color scale presented in Table 11.1.

Results

The results are shown in Table 22.1.

TABLE 22.1

Comparison of Application Procedures

| Vaginal Fluid Specimens | Dacron swabs | Cotton swabs |
|---|---|---|
| *Trichomonas*-positive (n = 22): | | |
| Scoring 0 | 3 | 5 |
| Scoring Trace | 1 | 1 |
| Scoring 1-2 | 6 | 6 |
| Scoring 3-4 | 4 | 2 |
| Scoring >4 | 8 | 8 |
| *Trichomonas*-negative (n = 49): | | |
| Scoring 0 | 41 | 45 |
| Scoring Trace | 7 | 4 |
| Scoring 1-2 | 1 | 0 |
| Scoring 3-4 | 0 | 0 |
| Scoring >4 | 0 | 0 |

The data in Table 22.1 show that the pink color produced on swabs containing vaginal fluid collected from women with trichomoniasis was somewhat more intense when the specimens were collected on Dacron swabs rather than cotton swabs. Twelve of 22 trichomonas-positive specimens collected on Dacron swabs scored three or higher, whereas ten of 22 trichomonas-positive specimens on cotton swabs scored three or higher. False-positive test results (scores of one or higher from trichomonas-negative specimens) were rare with either type of swab, but cotton swabs were less likely than Dacron swabs to produce even trace amounts of pink color from trichomonas-negative specimens. Of 49 trichomonas-negative specimens collected on cotton swabs, 45 produced no pink color at all (the swab tip was yellow), and four produced a trace amount of pink color (the swab tip was peach or orange). Of 49 trichomonas-negative specimens collected on Dacron swabs, 41 produced no pink color at all, seven produced a trace amount of pink color, and one produced a weak positive result (faint pink, scoring 1).

Interpretation

Either Dacron or cotton swabs can be used to collect vaginal fluid specimens for this diagnostic test for trichomoniasis. The test is not limited to a specific type of swab for specimen collection.

What is claimed is:

1. A test device for assaying a sample of vaginal fluid for the presence of a hydrolytic enzyme associated with *Trichomonas vaginalis*, said test device comprising
    a strip of solid porous material that allows aqueous liquids to pass therethrough while retaining particulate matter greater than 20 microns in diameter; and
    a conjugate comprising a chromogen covalently bonded to a substrate for said hydrolytic enzyme and releasable from said substrate by hydrolysis, said chromogen being a species that undergoes a detectable change upon hydrolytic release from said substrate, and said conjugate deposited in a region of said strip that is spatially separated from a sample application site on said strip by a length of said strip that is free of said conjugate, such that a sample of vaginal fluid applied to said application site migrates through said length to remove said particulate matter before reaching said conjugate.

2. A test device in accordance with claim 1 in which said solid porous material retains particulate matter greater than 10 microns in diameter.

3. A test device in accordance with claim 1 in which said solid porous material retains particulate matter greater than 1 micron in diameter.

4. A test device in accordance with claim 1 in which said chromogen is a member selected from the group consisting of indoxyl, chlorophenol red, and tetrabromophenolphthalein ethyl ester.

5. A test device in accordance with claim 1 in which said substrate is a peptide of 2 to 3 amino acids, the C terminus of which is bonded directly to said chromogen and is a member selected from the group consisting of lysine and arginine.

6. A test device in accordance with claim 5 in which the N-terminus of said peptide is protected against hydrolysis by an N blocking group selected from the group consisting of carbobenzoxy, benzoyl, t-butoxycarbonyl, and a D-amino acid.

* * * * *